(12) United States Patent
Shiratori et al.

(10) Patent No.: US 12,402,788 B2
(45) Date of Patent: Sep. 2, 2025

(54) OPHTHALMOLOGIC DEVICE AND METHOD FOR CONTROLLING SAME

(71) Applicant: Topcon Corporation, Tokyo (JP)

(72) Inventors: Takaaki Shiratori, Itabashi (JP); Takuya Oki, Itabashi (JP); Hiroyuki Aoki, Itabashi (JP); Yusuke Ono, Itabashi (JP)

(73) Assignee: TOPCON CORPORATION, Tokyo (JP)

( * ) Notice: Subject to any disclaimer, the term of this patent is extended or adjusted under 35 U.S.C. 154(b) by 732 days.

(21) Appl. No.: 17/730,188

(22) Filed: Apr. 27, 2022

(65) Prior Publication Data

US 2022/0248947 A1 Aug. 11, 2022

Related U.S. Application Data

(63) Continuation of application No. PCT/JP2020/037225, filed on Sep. 30, 2020.

(30) Foreign Application Priority Data

Oct. 29, 2019 (JP) .................................. 2019-196011

(51) Int. Cl.
*A61B 3/00* (2006.01)
*A61B 3/117* (2006.01)
*A61B 3/14* (2006.01)

(52) U.S. Cl.
CPC .......... *A61B 3/0083* (2013.01); *A61B 3/0025* (2013.01); *A61B 3/117* (2013.01); *A61B 3/14* (2013.01)

(58) Field of Classification Search
CPC ..... A61B 3/0083; A61B 3/0025; A61B 3/117; A61B 3/14; A61B 3/0075; A61B 3/11; A61B 3/0008; A61B 3/12

(Continued)

(56) References Cited

U.S. PATENT DOCUMENTS

2004/0114107 A1 6/2004 Mimura
2013/0188130 A1 7/2013 Inoue
(Continued)

FOREIGN PATENT DOCUMENTS

CN 103890641 A 6/2014
CN 107495919 A 12/2017
(Continued)

OTHER PUBLICATIONS

International Search Report issued Nov. 17, 2020 in International Application No. PCT/JP2020/037225, 2 pages.

(Continued)

*Primary Examiner* — Mohammed A Hasan
(74) *Attorney, Agent, or Firm* — XSENSUS LLP

(57) ABSTRACT

Provided are an ophthalmologic device and a method of controlling the same capable of accurately and reliably acquiring ocular characteristics of a subject eye. The ophthalmologic device includes: a face supporting unit configured to support a face of an examinee; an anterior ocular segment image acquiring unit configured to repeatedly acquire an anterior ocular segment image of the subject eye of the face supported by the face supporting unit; a pupil image detecting unit configured to detect a pupil image of the subject eye for each anterior ocular segment image based on the anterior ocular segment image repeatedly acquired by the anterior ocular segment image acquiring unit; and a determining unit configured to determine whether or not the face is properly supported by the face supporting unit based on a result of detection of the pupil image for each anterior ocular segment image by the pupil image detecting unit.

16 Claims, 14 Drawing Sheets

(58) Field of Classification Search
USPC .................................................. 351/208
See application file for complete search history.

(56) References Cited

U.S. PATENT DOCUMENTS

| | | | |
|---|---|---|---|
| 2014/0300866 A1 | 10/2014 | Fukuma et al. | |
| 2015/0085252 A1 | 3/2015 | Fujimura et al. | |
| 2016/0063326 A1* | 3/2016 | Yamashita | G02B 27/283 |
| | | | 348/78 |
| 2017/0347872 A1 | 12/2017 | Ozaki et al. | |
| 2019/0282092 A1 | 9/2019 | Nakamura | |
| 2020/0085293 A1* | 3/2020 | Fujikado | A61B 3/0091 |

FOREIGN PATENT DOCUMENTS

| | | | | |
|---|---|---|---|---|
| CN | 110269588 A | | 9/2019 | |
| EP | 3260040 A2 | | 12/2017 | |
| EP | 3733049 A1 | * | 11/2020 | ........... A61B 3/0008 |
| JP | 11-342110 A | | 12/1999 | |
| JP | 2012223435 A | | 11/2012 | |
| JP | 2013-150696 A | | 8/2013 | |
| JP | 2013-248376 A | | 12/2013 | |
| JP | 2014-161652 A | | 9/2014 | |
| JP | 2014-200678 A | | 10/2014 | |
| JP | 2018051340 A | | 4/2018 | |
| JP | 2019-165991 A | | 10/2019 | |
| JP | 7575216 B2 | * | 10/2024 | |

OTHER PUBLICATIONS

International Preliminary Report on Patentability issued May 3, 2022 in International Application No. PCT/JP2020/037225, 6 pages. (with English Translation of Written Opinion of the International Searching Authority).

Extended European search report issued on Jul. 27, 2023, in corresponding European patent Application No. 20882438.3, 8 pages.

Chinese Office Action issued Nov. 22, 2024, in corresponding Chinese Patent Application No. 202080074739.0, 18pp.

Japanese Office Action issued Nov. 17, 2023, in corresponding Japanese Patent Application No. 2019-196011, 10 pages.

Office Action issued on Mar. 11, 2024, in corresponding Japanese patent Application No. 2019-196011, 10 pages.

* cited by examiner

FIG.1
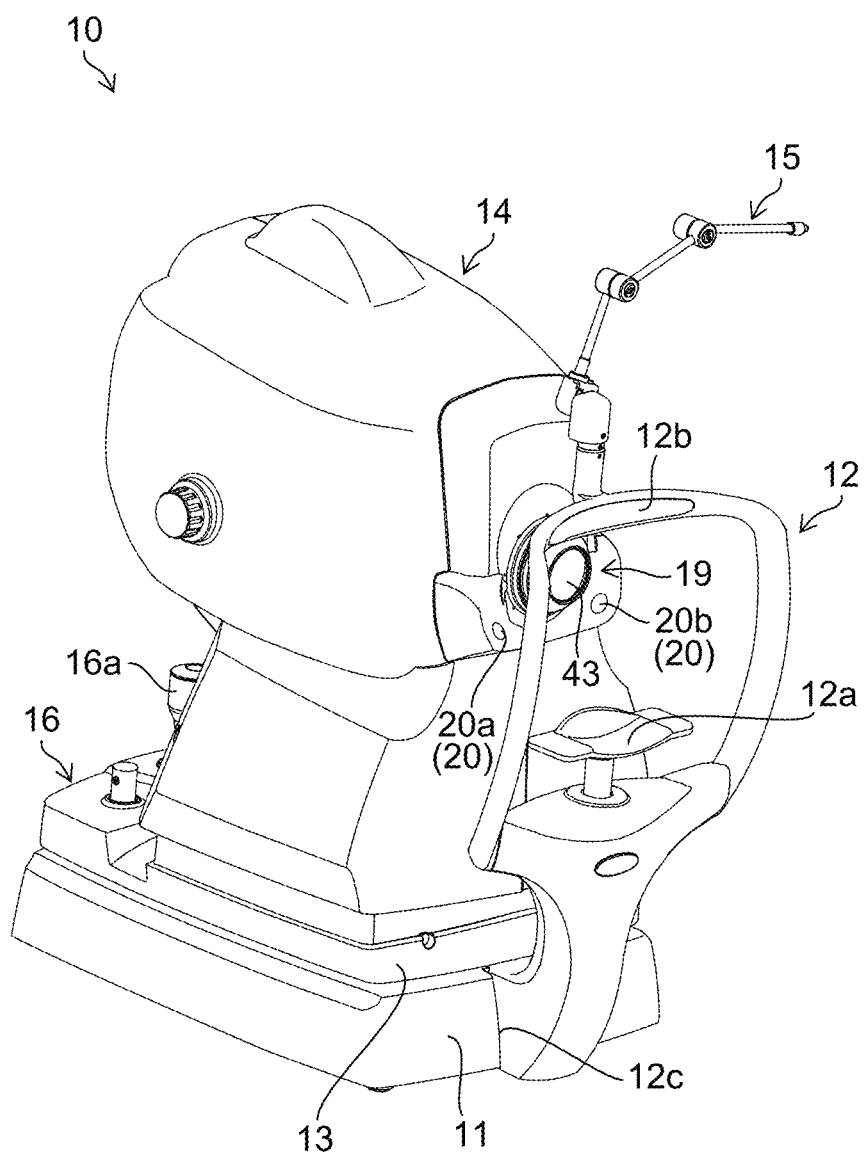
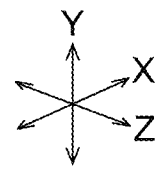

FIG.2
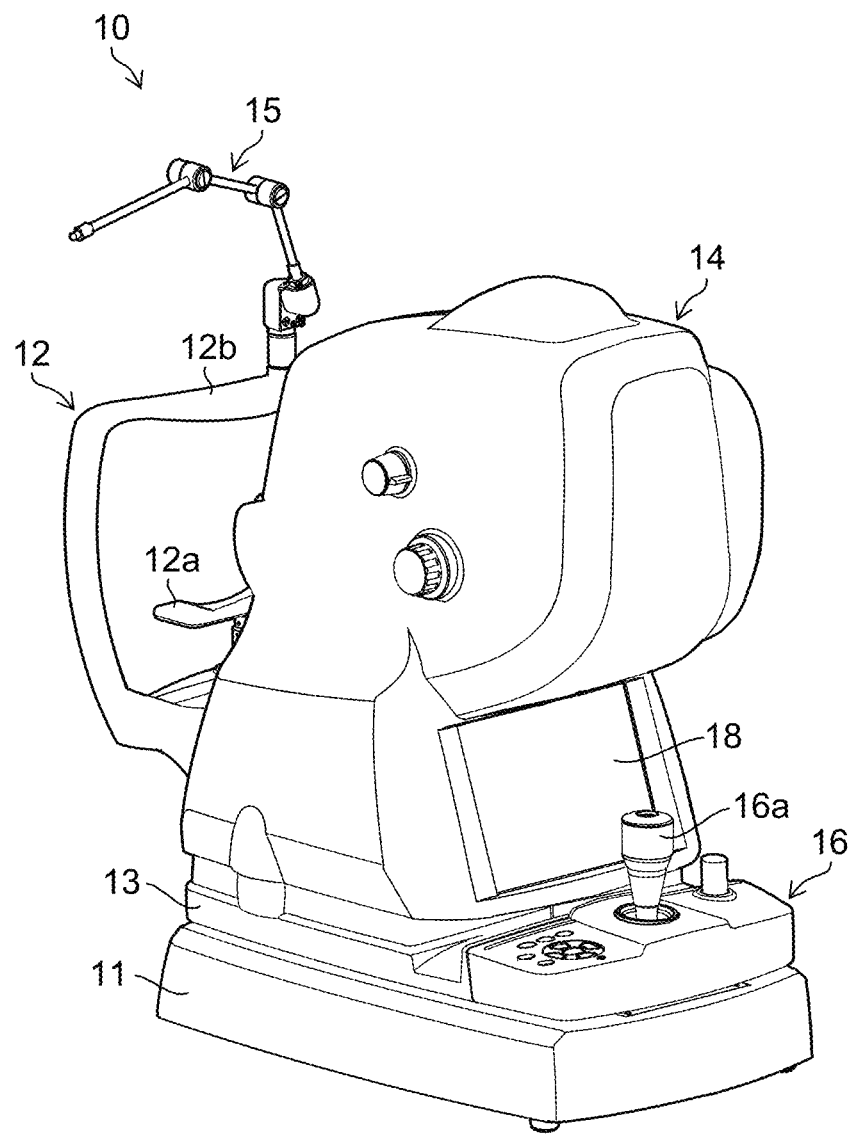
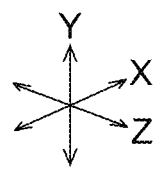

FIG.3
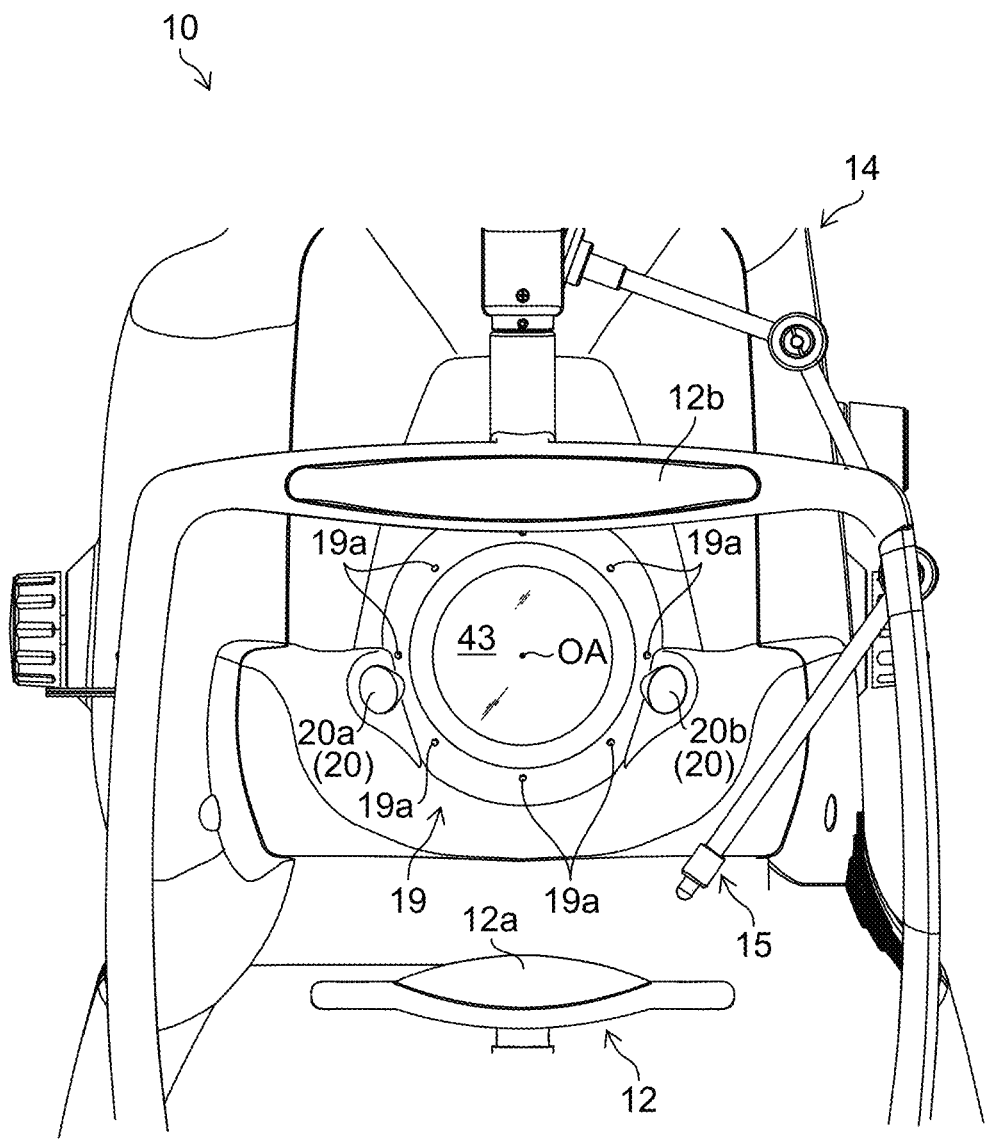
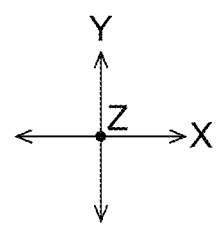

OPHTHALMOLOGIC DEVICE AND METHOD FOR CONTROLLING SAME

CROSS-REFERENCE TO RELATED APPLICATIONS

The present application is a Continuation of PCT International Application No. PCT/JP2020/037225 filed on Sep. 30, 2020, claiming priority under 35 U.S.C § 119(a) to Japanese Patent Application No. 2019-196011 filed on Oct. 29, 2019. Each of the above applications is hereby expressly incorporated by reference, in its entirety, into the present application.

BACKGROUND OF THE INVENTION

1. Field of the Invention

The present invention relates to an ophthalmologic device equipped with a face supporting unit configured to support an examinee's face and a method of controlling the ophthalmologic device.

2. Description of the Related Art

In ophthalmology, an ophthalmologic device acquires various ocular characteristics such as fundus photographic images, fundus tomographic images, ocular refractive power, an intraocular pressure, a number of corneal endothelial cells, and a corneal shape of a subject eye (measured, photographed, observed, and so forth). In this case, positioning, i.e., an alignment of a measurement head (optical system) of the ophthalmologic device to the subject eye, is extremely important from a viewpoint of accuracy, precision, and image quality of the ocular characteristics to be acquired. For this reason, the ophthalmologic device usually performs so-called full auto-alignment (hereinafter referred to as "auto-alignment"), which automatically performs alignment by detecting the relative position of the subject eye to the measurement head in a state where the examinee's face is supported by a face supporting unit such as a chin rest and moving the optical system with respect to the subject eye based on results of the detection.

For example, Patent Literature 1 and Patent Literature 2 disclose ophthalmologic devices that simultaneously photograph an anterior ocular segment of a subject eye from different directions from each other using a stereo camera positioned opposite to an examinee's face supported by a face supporting unit. In this ophthalmologic device, auto-alignment of the measurement head to the subject eye is performed based on the three-dimensional position of the subject eye obtained by analyzing the photographed image of the stereo camera.

CITATION LIST

Patent Literature 1: Japanese Patent Application Laid-Open No. 2013-248376
Patent Literature 2: Japanese Patent Application Laid-Open No. 2014-200678

SUMMARY OF THE INVENTION

Incidentally, in a case where the examinee's face is not properly supported by a face supporting unit such as a chin rest, for example, if the examinee's face is not in contact with the chin rest, the face (the subject eye) may move during the acquisition of ocular characteristics of the subject eye. As a result, the accuracy of the acquired ocular characteristics may become low or the acquisition of ocular characteristics may fail. For example, when photographing the fundus of a subject eye, if the face moves during the photographing, blurring and flare may occur in the fundus photographic image, or the photographing may fail. These problems cannot be solved no matter how high the accuracy of auto-alignment is made.

In view of such circumstances, the present invention aims to provide an ophthalmologic device capable of accurately and reliably acquiring ocular characteristics of a subject eye and a method of controlling the same ophthalmologic device.

In order to achieve the object of the present invention, an ophthalmologic device includes: a face supporting unit configured to support a face of an examinee; an anterior ocular segment image acquiring unit configured to repeatedly acquire an anterior ocular segment image of a subject eye of the face supported by the face supporting unit; a pupil image detecting unit configured to detect a pupil image of the subject eye for each anterior ocular segment image based on the anterior ocular segment image repeatedly acquired by the anterior ocular segment image acquiring unit: and a determining unit configured to determine whether or not the face is properly supported by the face supporting unit based on a result of detection of the pupil image for each anterior ocular segment image by the pupil image detecting unit.

According to the ophthalmologic device described above, acquisition of ocular characteristics of the subject eye can be performed in a state in which the face of the examinee is properly supported by the face supporting unit.

In the ophthalmologic device according to another aspect of the present invention, the anterior ocular segment image acquiring unit repeatedly acquires anterior ocular segment images from a plurality of cameras configured to photograph the subject eye from different directions, and the pupil image detecting unit includes: a first detecting unit configured to detect the pupil image from the anterior ocular segment image photographed by a first camera among the plurality of cameras; an estimating unit configured to estimate a presence range of the pupil image included in the anterior ocular segment image photographed by a second camera, which is different from the first camera among the plurality of cameras, the pupil image moving in response to involuntary eye movement of the subject eye, based on a result of detection by the first detecting unit; a second detecting unit configured to detect the pupil image from within the presence range of the anterior ocular segment image photographed by the second camera based on a result of estimation by the estimating unit; and a repetition controlling unit configured to repeatedly activate the first detecting unit, the estimating unit, and the second detecting unit each time when the anterior ocular segment image acquiring unit repeatedly acquires the anterior ocular segment images, and the determining unit determines whether or not the face is properly supported by the face supporting unit based on results of detection repeatedly performed by the second detecting unit. Accordingly, acquisition of ocular characteristics of the subject eye can be performed in a state in which the face of the examinee is properly supported by the face supporting unit.

In the ophthalmologic device according to another aspect of the present invention, the anterior ocular segment image acquiring unit performs: image acquisition processing for the first time for acquiring anterior ocular segment images from the first camera and the second camera which photograph the subject eye from directions different from each other; and image acquisition processing for the second and subsequent times for acquiring the anterior ocular segment image repeatedly from the second camera, and the pupil image detecting unit includes: a first detecting unit configured to detect the pupil image from the anterior ocular segment image acquired by the anterior ocular segment image acquiring unit from the first camera in the first image acquisition processing; an estimating unit configured to estimate a presence range of the pupil image included in the anterior ocular segment image acquired from the second camera by the anterior ocular segment image acquiring unit, the pupil image moving in response to the involuntary eye movement of the subject eye, based on a result of detection by the first detecting unit; a second detecting unit configured to detect the pupil image from within the presence range of the anterior ocular segment image acquired by the anterior ocular segment image acquiring unit from the second camera based on a result of estimation by the estimating unit; and a repetition controlling unit configured to repeatedly activate the second detecting unit each time when the anterior ocular segment image acquiring unit repeatedly acquires the anterior ocular segment image from the second camera in the image acquisition processing for the second and subsequent times, and the determining unit determines whether or not the face is properly supported by the face supporting unit based on results of detection repeatedly performed by the second detecting unit. Accordingly, it is possible to reduce time required for the determining unit to complete the determination.

In the ophthalmologic device according to another aspect of the present invention, the determining unit determines, based on the results of detection repeatedly performed by the second detecting unit, that the face is properly supported by the face supporting unit in a case where the detection of the pupil image in the presence range continues for a certain period of time, which is determined in advance, or more, and determines that the face is not properly supported by the face supporting unit in a case where the detection of the pupil image in the presence range does not continue for the certain period of time or more. Accordingly, acquisition of ocular characteristics of the subject eye can be performed in a state in which the face of the examinee is properly supported by the face supporting unit.

In the ophthalmologic device according to another aspect of the present invention, the estimating unit creates a template indicating the presence range and a shape of the pupil image from the anterior ocular segment image photographed by the first camera based on the result of detection by the first detecting unit, and the second detecting unit detects the pupil image from within the presence range of the anterior ocular segment image photographed by the second camera by template matching based on the template created by the estimating unit. This enables to simply and easily detect the pupil image from the anterior ocular segment image photographed by the second camera.

In the ophthalmologic device according to another aspect of the present invention, the anterior ocular segment image acquiring unit repeatedly acquires the anterior ocular segment image from one of a plurality of cameras that photograph the subject eye from directions different from each other. Thus, it is possible to determine whether or not the face is properly supported by the face supporting unit, using a single existing camera.

The ophthalmologic device according to another aspect of the present invention, further includes: an ocular characteristic acquiring unit configured to acquire ocular characteristics of the subject eye through an objective lens, and an anterior ocular segment observation system configured to photograph the subject eye through the objective lens, wherein the anterior ocular segment image acquiring unit repeatedly acquires the anterior ocular segment image from the anterior ocular segment observation system. Thus, it is possible to determine whether or not the face is properly supported by the face supporting unit, using a single existing camera, using an existing anterior ocular segment observation system.

The ophthalmologic device according to another aspect of the present invention, further includes: an ocular characteristic acquiring unit configured to acquire ocular characteristics of the subject eye through an objective lens, an ophthalmologic device main body configured to accommodate the ocular characteristic acquiring unit; a relative movement mechanism configured to move the ophthalmologic device main body with respect to the subject eye; a relative position detecting unit configured to detect a relative position of the subject eye relative to the ophthalmologic device main body based on the anterior ocular segment image acquired by the anterior ocular segment image acquiring unit; and an alignment controlling unit configured to drive the relative movement mechanism to perform alignment of the ophthalmologic device main body relative to the subject eye based on a result of detection by the relative position detecting unit. Thus, it is possible to perform processing for determining whether or not the face is properly supported by the face supporting unit and auto-alignment processing, in parallel.

The ophthalmologic device according to another aspect of the present invention, further includes a notifying unit configured to notify a result of determination by the determining unit in a case where the determining unit determines that the face is not properly supported by the face supporting unit. Thus, the examiner can be notified that the face is not properly supported by the face supporting unit.

The ophthalmologic device according to another aspect of the present invention, further includes a supporting position changing mechanism configured to change a face supporting position by the face supporting unit, wherein the notifying unit drives the supporting position changing mechanism to change the supporting position. Thus, the examinee can be also notified that the face is not properly supported by the face supporting unit.

The ophthalmologic device according to another aspect of the present invention, further includes a supporting position changing mechanism configured to change a face supporting position by the face supporting unit; a supporting position change controlling unit configured to drive the supporting position changing mechanism and change the face supporting position in a case where the determining unit determines that the face is not properly supported by the face supporting unit, and a redetermination controlling unit configured to repeatedly activate the anterior ocular segment image acquiring unit, the pupil image detecting unit, and the determining unit in a case where the face supporting position is changed by the supporting position changing mechanism. Thus, it is possible to properly support the face with the face supporting unit without any operations by the examiner or caution to the examiner, thereby reducing the examiner's time and effort.

In order to achieve the object of the present invention, a method of controlling an ophthalmologic device includes: an anterior ocular segment image acquisition step of repeatedly acquiring an anterior ocular segment image of a subject eye of a face supported by a face supporting unit configured to support the face of an examinee; a pupil image detection step of detecting a pupil image of the subject eye for each anterior ocular segment image based on the anterior ocular segment image repeatedly acquired by the anterior ocular segment image acquisition step; and a determination step of determining whether or not the face is properly supported by the face supporting unit based on a result of detection of the pupil image for each anterior ocular segment image by the pupil image detection step.

The present invention can accurately and reliably acquire ocular characteristics of a subject eye.

BRIEF DESCRIPTION OF THE DRAWINGS

FIG. 1 is a front perspective view of an ophthalmologic device according to a first embodiment, as seen from an examinee's side.

FIG. 2 is a rear perspective view of the ophthalmologic device as seen from the examiner's side.

FIG. 3 is a front view of a lens housing unit.

DESCRIPTION OF THE PREFERRED EMBODIMENTS

Figure 4:
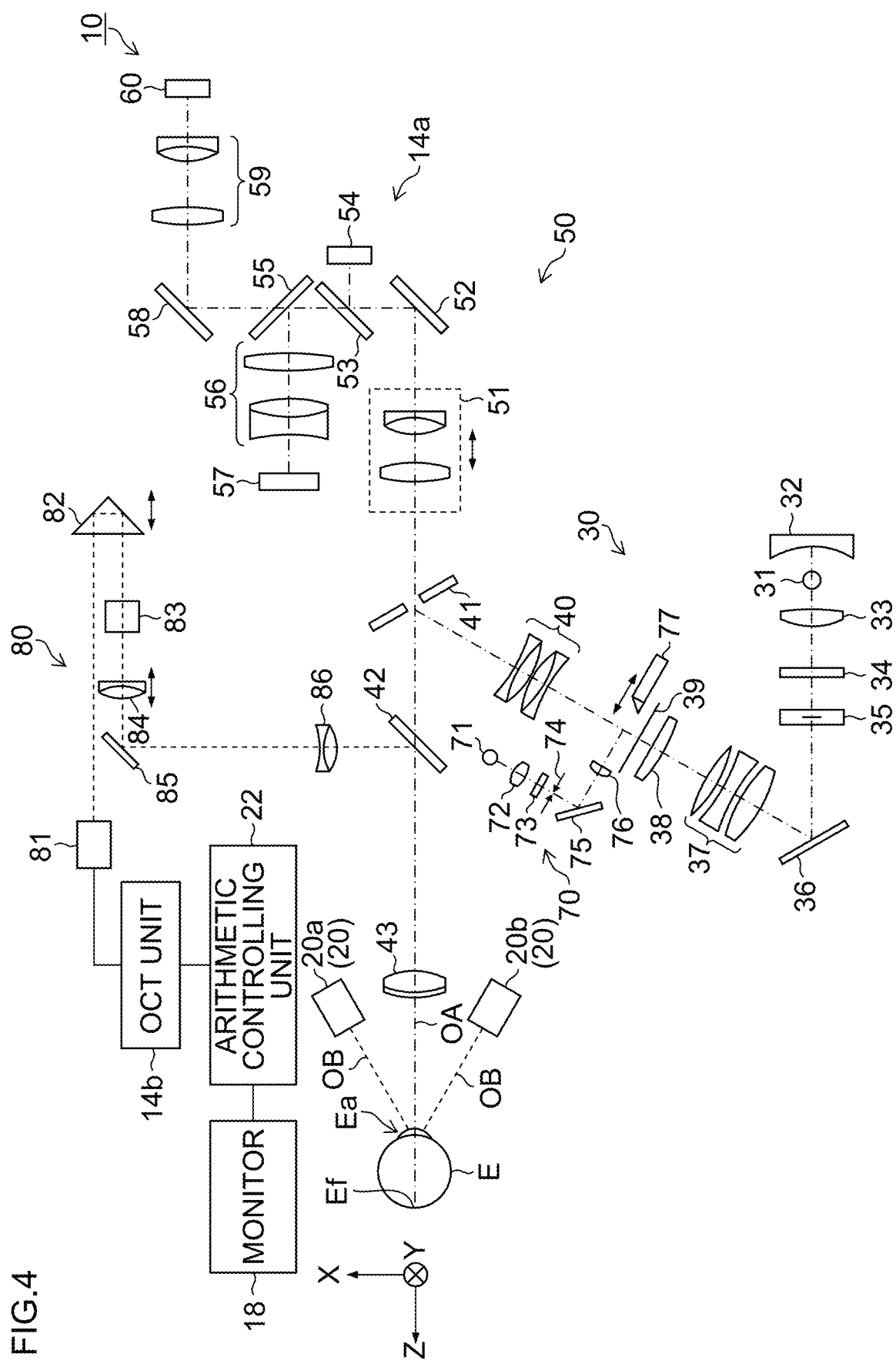
FIG. 4 is a schematic diagram illustrating an example of a configuration of a measurement head of the ophthalmologic device.

[Overall Configuration of Ophthalmologic Device According to First Embodiment]

FIG. 1 is a front perspective view of an ophthalmologic device 10 according to a first embodiment, as seen from an examinee's side. FIG. 2 is a rear perspective view of the ophthalmologic device 10 as seen from an examiner's side. An X direction in the Figure is a left-right direction (the eye width direction of the subject eye E illustrated in FIG. 4) with respect to the examinee, a Y direction is an up-down direction, and a Z direction is a front-rear direction (also referred to as an operation distance direction) parallel to a front direction approaching the examinee and a rear direction moving away from the examinee.

As illustrated in FIGS. 1 and 2, an ophthalmologic device 10 is a combined machine including a fundus camera and an optical coherence tomography (OCT) configured to acquire an OCT image, which is a cross-sectional image, using an optical coherence tomography. The ophthalmologic device 10 acquires (measures, photographs, observes, and so forth) a fundus photographic image and an OCT image of a fundus Ef (see FIG. 4) as ocular characteristics of the subject eye E (see FIG. 4). The ophthalmologic device 10 has a base 11, a face supporting unit 12, a mount 13, and a measurement head 14.

The mount 13 is provided on the base 11. In the base 11, an arithmetic controlling unit 22 (see FIG. 4) and the like, described below, are stored.

The face supporting unit 12 is provided integrally with the base 11 at a position on the front side in the Z direction of the measurement head 14. The face supporting unit 12 has a chin rest 12a and a forehead fit 12b which are positionally adjustable in the Y direction (up-down direction) and supports the examinee's face at a position facing the main body of the ophthalmologic device such as the measurement head 14 (an objective lens 43 described below).

The face supporting unit 12 is provided with a motorized lifting mechanism 12c, which corresponds to the supporting position changing mechanism of the present invention. The motorized lifting mechanism 12c is a known actuator such as a motor driving mechanism and changes the supporting position of the examinee's face by moving the chin rest 12a and the forehead fit 12b in the Y direction under the control of the arithmetic controlling unit 22 (see FIG. 4) described below.

Furthermore, the face supporting unit 12 is provided with an external fixation light 15. The external fixation light 15 has a light source that emits a fixation light, and a position of the light source and a direction of emission of the fixation light can be adjusted arbitrarily. The external fixation light 15 is used for external fixation. External fixation is a method of visual fixation to rotate the subject eye E (see FIG. 4) in an arbitrary direction by adjusting the position of the light source of the external fixation light 15, or to rotate the subject eye E more largely than a case of internal fixation. Alternatively, the external fixation adjusts the direction of the subject eye E by guiding a visual line of the subject eye E or a fellow eye, when the internal fixation cannot be performed.

The mount 13 is movable in the X direction and Z direction (front-rear direction and left-right direction) with respect to the base 11. An operating unit 16 is provided on the mount 13. The measurement head 14 is provided on the mount 13 so as to be movable in the Y direction.

A motorized driving mechanism 17 (see FIG. 4), which corresponds to the relative movement mechanism of the present invention, is provided on the mount 13. The motorized driving mechanism 17 is a known actuator such as a motor driving mechanism and moves the mount 13 in the XZ directions and moves the measurement head 14 in the Y direction under the control of the arithmetic controlling unit 22 (see FIG. 4) described below. This moves the measurement head 14 with respect to the subject eye E in the XYZ directions.

The operating unit 16 is provided on the mount 13 at a position on the rear side (examiner's side) of the measurement head 14 in the Z direction. In the operating unit 16, in addition to operation buttons for performing various operations of the ophthalmologic device 10, an operation lever 16a is provided.

The operation lever 16a is an operation member for manually moving the measurement head 14 in each of the XYZ directions. For example, when the operation lever 16a is tilted in the Z direction (front-back direction) or the X direction (left-right direction), the above-mentioned motorized driving mechanism 17 (see FIG. 4) moves the measurement head 14 in the Z direction or the X direction. When the operation lever 16a is rotated around a longitudinal axis thereof, the motorized driving mechanism 17 moves the measurement head 14 is in the Y direction (up-down direction) according to the direction of the rotation operation.

The measurement head 14 constitutes the main body of the ophthalmologic device of the present invention. A fundus camera unit 14a and an OCT unit 14b illustrated in FIG. 4 below are built in the measurement head 14. A monitor 18 is provided on a rear surface of the measurement head 14, on a rear side (examiner's side) in the Z direction. The lens housing 19 is provided in front of the measurement head 14 on the front side (examinee's side) in the Z direction.

As the monitor 18, a touch panel type liquid crystal display device, for example, is used. This monitor 18 displays various imaging data of the subject eye E (see FIG. 4) and input screens for various setting operations.

FIG. 3 is a front view of the lens housing 19. As illustrated in FIG. 3, the lens housing 19 constitutes a part of the fundus camera unit 14a (see FIG. 4) and houses an objective lens 43 having an optical axis OA parallel to the Z direction. Also, the lens housing 19 includes eight fixation holes 19a (also referred to as fixation lights) which are disposed at an equal interval along the circumferential direction of the objective lens 43 so as to surround the objective lens 43. Each of the fixation holes 19a selectively emits a fixation light in the Z direction in response to an operation at the operating unit 16.

Each fixation hole 19a is used for peripheral fixation and for photographing the corner angle (edge of the iris) of the subject eye E (see FIG. 4). Peripheral fixation is a method of visual fixation to greatly rotate the subject eye E in desired directions by selectively lighting each of the fixation holes 19a.

In addition, a stereo camera 20, which corresponds to a plurality of cameras of the present invention, is provided in front of the measurement head 14 in the vicinity of the lens housing 19. The stereo camera 20 has a first camera 20a and a second camera 20b. The first camera 20a and the second camera 20b are disposed so as to interpose the objective lens 43 therebetween, from the left and right of the objective lens 43, on a surface of the measurement head 14 (the surface facing the subject eye E) on the front side in the Z-direction.

FIG. 4 is a schematic diagram illustrating an example of a configuration of a measurement head 14 of the ophthalmologic device 10. As illustrated in FIG. 4, the measurement head 14 includes a fundus camera unit 14a, an OCT unit 14b, the stereo camera 20, and the arithmetic controlling unit 22.

The fundus camera unit 14a has an optical system almost similar to that of a conventional fundus camera and acquires (photographs) various observation images of the anterior ocular segment Ea or the like of the subject eye E as well as a fundus photographic image of the fundus Ef as ocular characteristics of the subject eye E through the objective lens 43. The OCT unit 14b acquires an OCT image of the fundus Ef as ocular characteristics of the subject eye E through the objective lens 43 and an optical system of part of the fundus camera unit 14a. Therefore, the fundus camera unit 14a functions as an ocular characteristic acquiring unit and an anterior ocular segment observation system of the present invention. The OCT unit 14b functions as the ocular characteristic acquiring unit of the present invention.

The arithmetic controlling unit 22 is housed in the base 11 (or possibly in the measurement head 14) and is an arithmetic processing device such as a personal computer or the like that performs various arithmetic processing and control processing.

[Fundus Camera Unit]

The fundus camera unit 14a includes an illumination optical system 30 and an imaging optical system 50 as optical systems for acquiring an observation image of the anterior ocular segment Ea or the like and a fundus photographic image, which is a two-dimensional image representing a surface form (surface shape) of the fundus Ef.

The illumination optical system 30 irradiates the fundus Ef with illumination light. The imaging optical system 50 guides a light reflected from the fundus, which is an illumination light reflected by the fundus Ef, to image pickup devices 57, 60 which are of CMOS (Complementary Metal Oxide Semiconductor) type or CCD (Charge Coupled Device) type, for example. In addition, the imaging optical system 50 guides a signal light output from the OCT optical system 80 (OCT unit 14b) to the fundus Ef and guides the signal beam reflected from the fundus Ef to the OCT optical system 80.

The illumination optical system 30 includes an observation light source 31, a reflection mirror 32, a focusing lens 33, a visible cut filter 34, a photographing light source 35, mirror 36, relay lenses 37, 38, an aperture 39, a relay lenses 40, a perforated mirror 41, a dichroic mirror 42, an objective lens 43, and the like.

In addition to the objective lens 43, the dichroic mirror 42, and the perforated mirror 41 described above, the imaging optical system 50 includes a focusing lens 51, a mirror 52, a half mirror 53, an optotype display 54, a dichroic mirror 55, a focusing lens 56, an image pickup device 57, a mirror 58, a focusing lens 59, an image pickup device 60, and the like.

The observation light source 31 is, for example, a halogen lamp or an LED (light emitting diode) and emits observation illumination light. The observation illumination light emitted from the observation light source 31 is reflected by the reflection mirror 32, passes through the focusing lens 33, and passes through the visible cut filter 34 to become near-infrared light. The observation illumination light passed through the visible cut filter 34 is once focused on the vicinity of the photographing light source 35, is reflected by the mirror 36, and passes through the relay lenses 37, 38, the aperture 39, and the relay lenses 40. Then, the observation illumination light is reflected at the peripheral part (region around the hole) of the perforated mirror 41, passes through the dichroic mirror 42, and is further refracted by the objective lens 43 to illuminate the fundus Ef.

The light reflected from the fundus of the observation illumination light, is refracted by the objective lens 43, passes through the dichroic mirror 42, the hole formed in the center region of the perforated mirror 41, and the focusing lens 51, and then is reflected by the mirror 52. Further, the light reflected from the fundus passes through the half mirror 53 and then is reflected by the dichroic mirror 55, so as to form an image on the light receiving surface of the image pickup device 57 by the focusing lens 56. The image pickup device 57 captures (receives) the light reflected from the fundus and outputs an imaging signal to the arithmetic controlling unit 22 described below. The arithmetic controlling unit 22 causes the monitor 18 to display various observation images based on the image signal output from the image pickup device 57. Note that, in a case where the focus of the imaging optical system 50 is adjusted to the anterior ocular segment Ea of the subject eye E, the observation image of the anterior ocular segment Ea is displayed on the monitor 18. On the other hand, in a case where the focus of the imaging optical system 50 is adjusted to the fundus Ef, the observation image of the fundus Ef is displayed on the monitor 18.

The photographing light source 35 emits photographing illumination light. A xenon lamp or an LED light source is used as the photographing light source 35, for example. The photographing illumination light emitted from the photographing light source 35 irradiates the fundus Ef through the same path as the observation illumination light previously described. The light reflected from the fundus of the photographing illumination light is led to the dichroic mirror 55 through the same path as the light reflected from the fundus of the observation illumination light, passes through the dichroic mirror 55, and then is reflected by the mirror 58, so as form an image on the light receiving surface of the image pickup device 60 by the focusing lens 59.

The image pickup device 60 captures (receives) the light reflected from the fundus and outputs an imaging signal to the arithmetic controlling unit 22 described below. The arithmetic controlling unit 22 causes the monitor 18 to display fundus photographic image based on the imaging signal output from the image pickup device 60. The monitor 18 displaying the various observation images and the monitor 18 displaying the fundus photographic image may be the same or may be provided separately from each other.

The optotype display 54 is used for internal fixation to project the fixation light of the fixation target (bright spot image) to the subject eye E through the objective lens 43. As the optotype display 54, for example, a dot matrix liquid crystal display (LCD) and a matrix light emitting diode (LED) may be used. The optotype display 54 displays a fixation target. In addition, the display mode (shape, and so forth.) and display position of the fixation target may be arbitrarily set in the optotype display 54.

The fixation light of the fixation target displayed on the optotype display 54 is partly reflected by the half mirror 53, then is projected onto the subject eye E via the mirror 52, the focusing lens 51, a hole in a perforated mirror 41, a dichroic mirror 42, and objective lens 43. As a result, a fixation target, a visual acuity measurement target, and so forth are presented to the subject eye E through the objective lens 43.

The fundus camera unit 14a includes a focusing optical system 70. The focusing optical system 70 creates a split indicator for focusing (focusing) on the fundus Ef. The focusing optical system 70 includes, in addition to the previously described objective lens 43, the dichroic mirror 42, and the perforated mirror 41, an LED 71, a relay lens 72, a split indicator plate 73, a two-hole aperture 74, a mirror 75, a focusing lens 76, and a reflecting rod 77.

The reflecting surface of the reflecting rod 77 is set in the optical path of the illumination optical system 30 in a case where focus adjustment by the focusing optical system 70 is performed. The focus light emitted from the LED 71 passes through the relay lens 72, is separated into two light fluxes by the split indicator plate 73, then forms an image once on the reflecting surface of the reflecting rod 77 via the two-hole aperture 74, the mirror 75, and the focusing lens 76, and is reflected on the reflecting surface toward the relay lenses 40. Further, the focus light is projected on the fundus Ef via the relay lenses 40, the perforated mirror 41, the dichroic mirror 42, and the objective lens 43.

The light reflected from the fundus of the focus light passes through the objective lens 43, the dichroic mirror 42, and the hole of the perforated mirror 41, then passes through the focusing lens 51, the mirror 52, the half mirror 53, the dichroic mirror 55 and the focusing lens 56, and is then photographed by the image pickup device 57. The image pickup device 57 photographs the light reflected from the fundus of the focus light and outputs an imaging signal. This causes the split indicator to be displayed on the monitor 18 together with the observed image. The arithmetic controlling unit 22 described below analyzes the position of the split indicator and moves the focusing lens 51 and the like to automatically adjust the focus as conventionally done. The focus may also be adjusted manually by the examiner based on the split indicator displayed on the monitor 18.

The dichroic mirror 42 diverges the optical path of the OCT optical system 80 from the optical path for fundus photography. The dichroic mirror 42 reflects light in the wavelength band used for OCT measurement and transmits light for fundus photography. On the optical path of this OCT optical system 80, in an order starting from the OCT unit 14b side, a collimator lens unit 81, an optical path length changing unit 82, a galvano scanner 83, a focusing lens 84, a mirror 85, a relay lens 86 are provided.

The optical path length changing unit 82 includes, for example, a corner cube and a mechanism for moving the corner cube. The optical path length changing unit 82 is movable in a direction of an arrow illustrated in FIG. 4 to change the optical path length of the OCT optical system 80. The change of the optical path length is used to correct the optical path length according to the ocular axis length of the subject eye E and to adjust the interference state.

The galvano scanner 83 changes the direction of travel of the signal light passing through the optical path of the OCT optical system 80. This allows the fundus Ef to be scanned with signal light. The galvano scanner 83 includes, for example, a galvano mirror for scanning the signal light in the X direction, a galvano mirror for scanning the signal light in the Y direction, and a mechanism for driving these mirrors independently. This allows scanning with the signal light in any direction on the XY plane.

[Oct Unit]

The OCT unit 14b includes an interferometric optical system used for acquiring the OCT image of the fundus Ef. In the same manner as a publicly-known OCT apparatus, the OCT unit 14b divides the low-coherence light into a reference light and a signal light, causes the signal light having passed through the fundus Ef to interfere with the reference light having passed through the reference light path to generate an interference light, and detects a spectral component of the interference light. The result of detection (detection signal) by the OCT unit 14b is output to the arithmetic controlling unit 22. Since the specific configuration of the OCT unit 14b is a known technology (see, for example, PTL 1 described above), the specific description is omitted here.

[Stereo Camera]

The first camera 20a and the second camera 20b that constitute the stereo camera 20 photograph the anterior ocular segment Ea simultaneously (including substantially simultaneously) and continuously (take a motion picture) from directions different from each other. In this embodiment, the first camera 20a and the second camera 20b simultaneously and continuously photograph the anterior ocular segment Ea from the left and right directions. The signs OB in the drawing designate the optical axes of the first camera 20a and the second camera 20b.

The first camera 20a continuously photographs the anterior ocular segment Ea from one of the left and right directions, and outputs an anterior ocular segment image D1, which is an observation image of the anterior ocular segment Ea (see FIG. 5) to the arithmetic controlling unit 22. The second camera 20b continuously photographs the anterior ocular segment Ea from the other of the left and right directions, and outputs an anterior ocular segment image D2, which is an observation image of the anterior ocular segment Ea (see FIG. 5) to the arithmetic controlling unit 22. Note that the arrangement of the first camera 20a and the second camera 20b may be reversed. These anterior ocular segment images D1 and D2 are used for the face support determination (also referred to as the chin rest determination), which is a determination of whether or not the examinee's face is properly (appropriately) supported by the face supporting unit 12, and for the auto-alignment of the measurement head 14 to the subject eye E.

[Arithmetic Controlling Unit]

Figure 5:
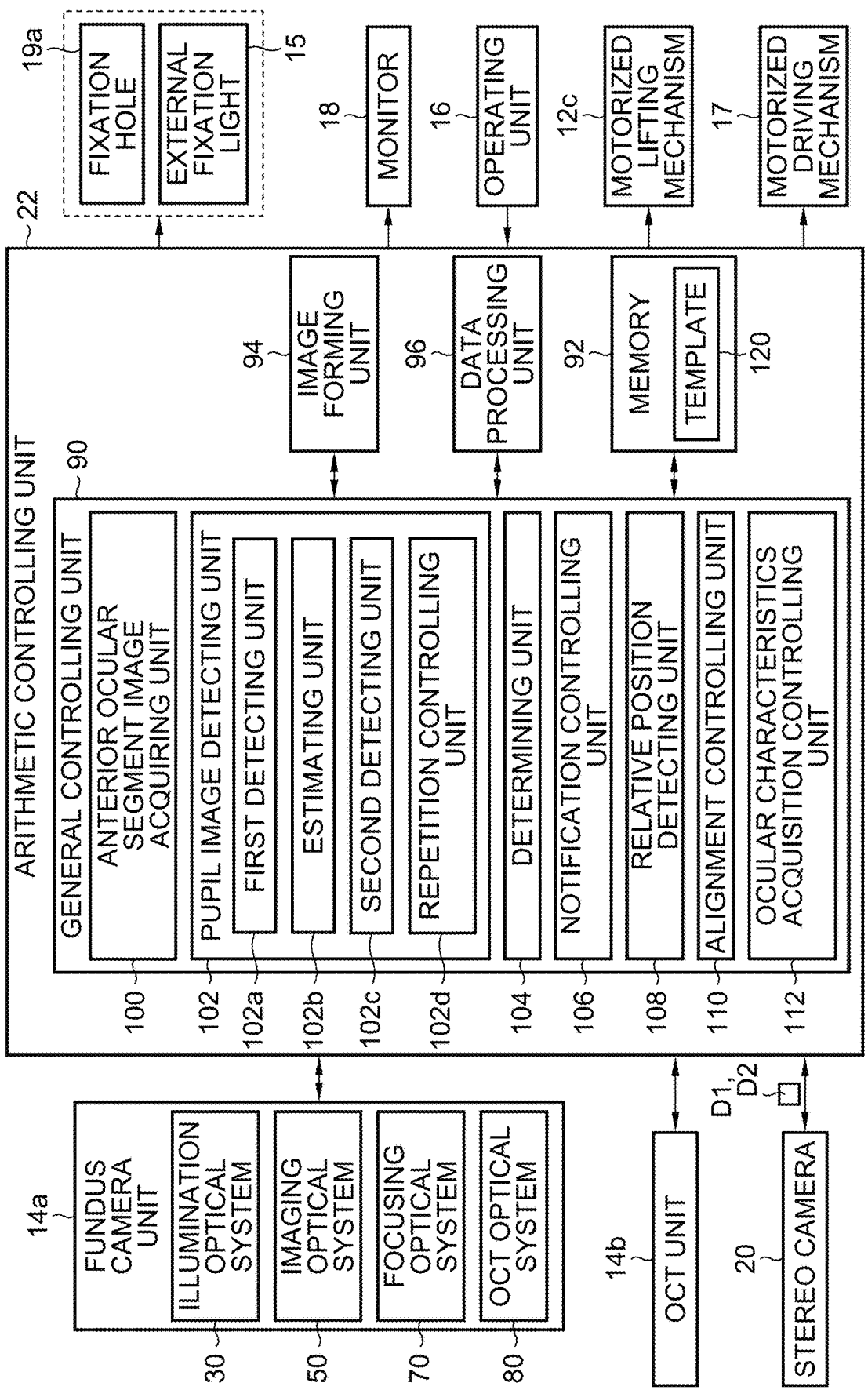
FIG. 5 is a functional block diagram of an arithmetic controlling unit according to the first embodiment.

FIG. 5 is a functional block diagram of the arithmetic controlling unit 22 according to the first embodiment. As illustrated in FIG. 5, the arithmetic controlling unit 22 has a general controlling unit 90, a memory 92, an image forming unit 94, and a data processing unit 96, and the like. In addition, the previously described the motorized lifting mechanism 12c, the fundus camera unit 14a, the OCT unit 14b, the external fixation light 15, the operating unit 16, the motorized driving mechanism 17, the monitor 18, the fixation holes 19a, the stereo camera 20, and so forth are connected to the arithmetic controlling unit 22.

The memory 92 stores a control program to be performed by the general controlling unit 90, image data of the OCT image, image data of the fundus image, subject eye information (including examinee information), and so forth. The memory 92 also stores the template 120, which will be described below.

The image forming unit 94, together with the OCT unit 14b, constitutes the ocular characteristic acquiring unit of the present invention. The image forming unit 94 analyzes the detection signal input from the OCT unit 14b to form an OCT image of the fundus Ef. Note that the specific method of forming the OCT image is the same as that of the conventional OCT system, so the explanation is omitted here. The data processing unit 96 performs image processing or the like on the OCT image formed by the image forming unit 94, the fundus photographic image and various observation images acquired by the fundus camera unit 14a, and the anterior ocular segment images D1 and D2 acquired by the stereo camera 20, and so forth.

The general controlling unit 90 integrally controls the operation of each unit of the ophthalmologic device 10. The general controlling unit 90 performs the face support determination based on the anterior ocular segment images D1 and D2 input from the stereo camera 20. In a case where it is determined that the face is properly supported by the face supporting unit 12, the general controlling unit 90 performs auto-alignment based on images of the anterior ocular segment D1 and D2. After the auto-alignment, the general controlling unit 90 controls the fundus camera unit 14a and the OCT unit 14b to acquire fundus photographic images and OCT images of the fundus Ef, and so forth. In FIG. 5, only the functions related to face support determination, auto-alignment, and acquisition of ocular characteristics (fundus photographic image and OCT image) of the subject eye E are illustrated. Because other functions are of known technology, specific illustrations are omitted.

The functions of the general controlling unit 90 can be realized using various types of processors (processors). The various types of processors include Central Processing Units (CPU), Graphics Processing Units (GPU), Application Specific Integrated Circuits (ASIC), and programable logic devices (for example, Simple Programmable Logic Device (SPLD), Complex Programmable Logic Device (CPLD), and Field Programmable Gate Arrays (FPGA)) and so forth. Note that various functions of the general controlling unit 90 may be implemented in one processor or may be implemented in a plurality of processors of the same type or of different type.

When acquiring the ocular characteristics (fundus photographic image and OCT image) of the subject eye E, the general controlling unit 90 functions as the anterior ocular segment image acquiring unit 100, the pupil image detecting unit 102, the determining unit 104, the notification controlling unit 106, relative position detecting unit 108, an alignment controlling unit 110, and the ocular characteristics acquisition controlling unit 112. Components described as the "~unit" of the arithmetic controlling unit 22 may be re placed by "~circuit", "~apparatus", or "~equipment". In other words, those described as the "~unit" may be composed of a firmware, software, and hardware or a combination thereof.

[Face Support Determination]

The anterior ocular segment image acquiring unit 100 is used for both face support determination and auto-alignment, and functions as image input interface wired or wirelessly connected to each of the first camera 20a and the second camera 20b of the stereo camera 20. The anterior ocular segment image acquiring unit 100 acquires anterior ocular segment images D1 and D2 respectively from the first camera 20a and the second camera 20b which continuously photograph the anterior ocular segment Ea. In addition, the anterior ocular segment image acquiring unit 100 repeatedly outputs the acquired anterior ocular segment images D1 and D2 to the pupil image detecting unit 102 and the relative position detecting unit 108.

The pupil image detecting unit 102 is used for face support determination. The pupil image detecting unit 102 repeatedly performs a processing for detecting a pupil image 116 (see FIG. 6), which is the image of the pupil of the subject eye E, from the anterior ocular segment images D1 and D2 input repeatedly from the anterior ocular segment image acquiring unit 100, for each of the anterior ocular segment images D1 and D2. Unlike the processing for detecting the pupil image 116 performed by the relative position detecting unit 108 for auto-alignment, the processing for detecting the pupil image 116 by the pupil image detecting unit 102 is a simple processing because it requires only detection of the pupil image 116 within a range of the involuntary eye movement of the subject eye E.

The pupil image detecting unit 102 functions as a first detecting unit 102a, an estimating unit 102b, a second detecting unit 102c, and a repetition controlling unit 102d.

Figure 6:
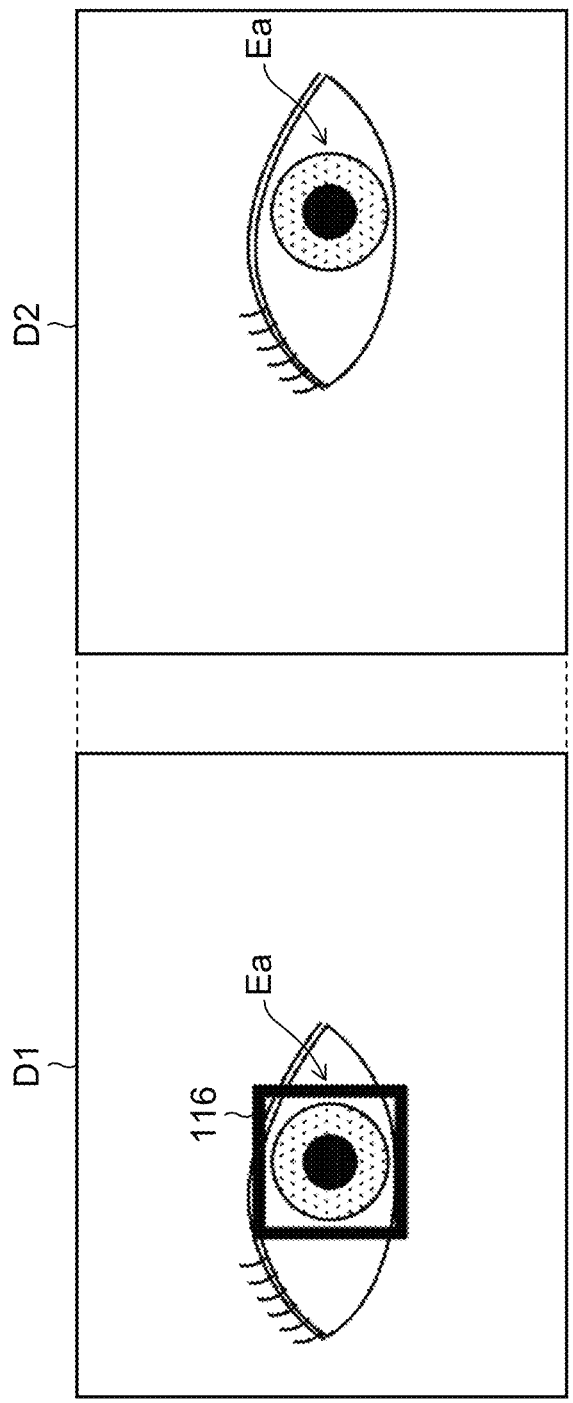
FIG. 6 is an explanatory drawing for describing a processing for detecting a pupil image by a first detecting unit.

FIG. 6 is an explanatory drawing for describing the processing for detecting the pupil image 116 by the first detecting unit 102a. As illustrated in FIG. 6 and previously described in FIG. 5, the first detecting unit 102a detects the pupil image 116 from the anterior ocular segment image D1 photographed by the first camera 20a. Note that the first camera 20a and the second camera 20b may be designated such that the one that captures a clearer image of the anterior ocular segment Ea is designated as the "first camera 20*a*", and the other one is designated as the "second camera 20*b*".

The first detecting unit 102*a*, for example, performs known binarization processing, labeling processing, and filtering processing by circularity, on the full-size anterior ocular segment image D1. The labeling processing is processing for labeling consecutive white or black pixels in each pixel of the binarized anterior ocular segment image D1 with the same label (assigning the same number). Filtering processing by circularity is processing for detecting regions where the circularity exceeds a predetermined value determined in advance from the anterior ocular segment image D1 after the labeling processing. This allows the first detecting unit 102*a* to detect the pupil image 116 from within the anterior ocular segment image D1, and outputs the result of detection indicating the shape and position of the pupil image 116 to the estimating unit 102*b*.

Note that the method of detecting the pupil image 116 from the anterior ocular segment image D1 by the first detecting unit 102*a* is not limited to the method described above (binarization processing, labeling processing, and filtering processing), and any known method may be used. In particular, a simple and detectable method is preferable.

Figure 7:
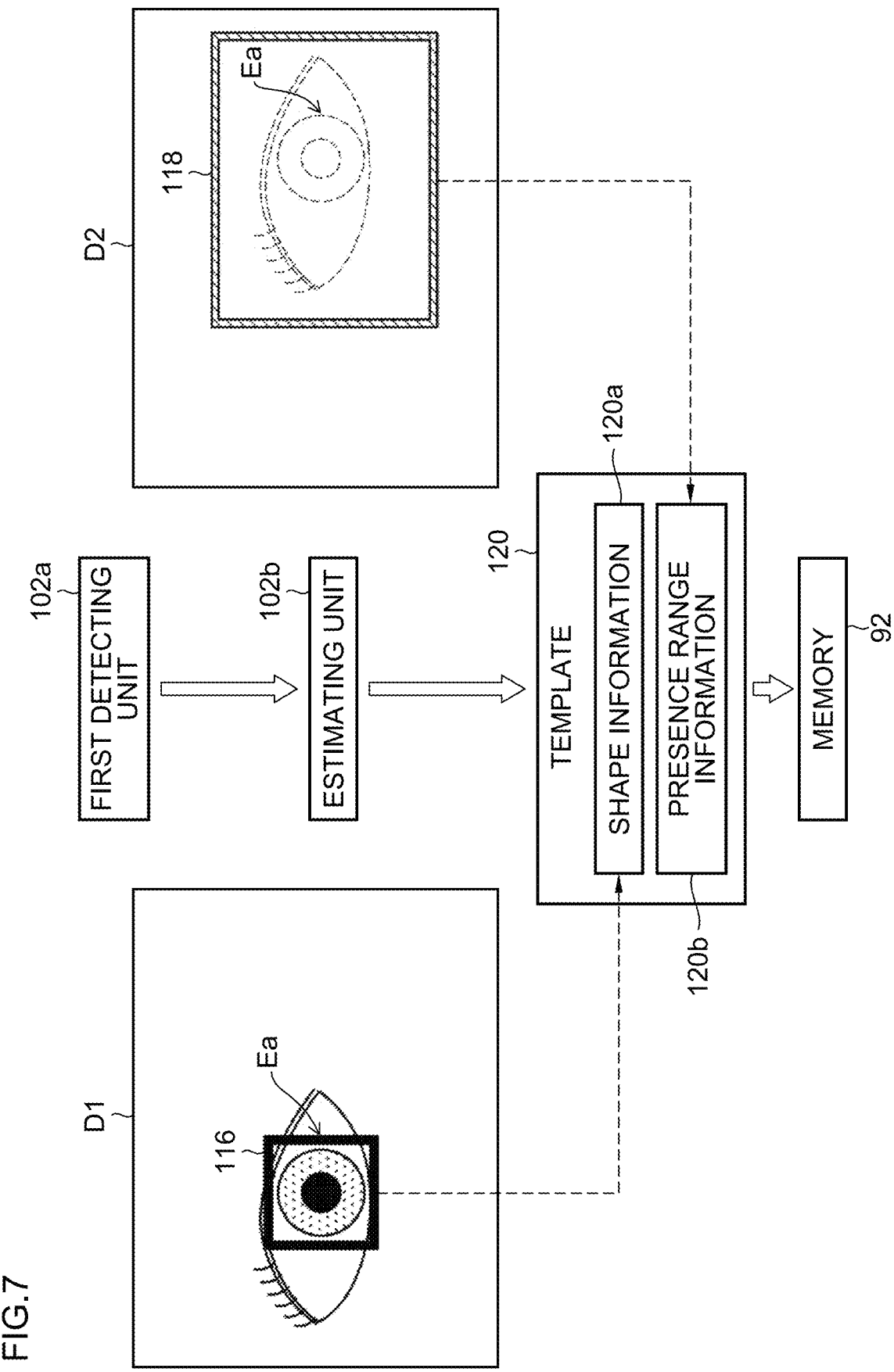
FIG. 7 is an explanatory drawing for describing creation of a template by an estimating unit.

FIG. 7 is an explanatory drawing illustrating creation of a template 120 by the estimating unit 102*b*. As illustrated in FIG. 7 and FIG. 5, the estimating unit 102*b* creates the template 120 used for detecting the pupil image 116 (template matching) in the anterior ocular segment image D2 by the second detecting unit 102*c* described later based on the result of detection of the pupil image 116 in the anterior ocular segment image D1 by the first detecting unit 102*a*.

Specifically, the estimating unit 102*b* estimates the shape of the pupil image 116 in the anterior ocular segment image D2 based on the shape of the pupil image 116 in the anterior ocular segment image D1 detected by the first detecting unit 102*a* and creates shape information 120*a* corresponding to the result of estimation.

In addition, the estimating unit 102*b* estimates a presence range 118 of the pupil image 116 in the anterior ocular segment image D2 based on the position of the pupil image 116 in the anterior ocular segment image D1 detected by the first detecting unit 102*a* and creates presence range information 120*b* corresponding to the result of estimation. The presence range 118 indicates a range in which the pupil image 116, which moves in the anterior ocular segment image D2 in response to the involuntary eye movement of the subject eye E, is present. In the illustration in FIG. 7 (as well as FIG. 8 described below), the presence range 118 is exaggerated compared to the actual one in order to prevent complication of the drawing.

Here, the method of generating the presence range information 120*b* is not limited. The positional relationship between the first camera 20*a* and the second camera 20*b* and the photographing magnifications (reproduction ratios) of the first camera 20*a* and the second camera 20*b*, are known. Therefore, the estimating unit 102*b* can estimate the position of the pupil image 116 within the anterior ocular segment image D2 based on the position of the pupil image 116 within the anterior ocular segment image D1 detected by the first detecting unit 102*a*. In addition, the degree to which the pupil image 116 is displaced within the anterior ocular segment image D2 in response to the involuntary eye movement of the subject eye E can also be determined in advance by experiment or simulation. Therefore, the estimating unit 102*b* can create the presence range information 120*b* by estimating the presence range 118 based on the result of detection of the first detecting unit 102*a*, the positional relationship between the first camera 20*a* and the second camera 20*b*, and the photographing magnifications thereof, and the amount of displacement of the pupil image 116 according to the involuntary eye movement of the subject eye E.

Then, the estimating unit 102*b* creates the template 120 including the shape information 120*a* and the presence range information 120*b*, and stores the template 120 in the memory 92.

Figure 8:
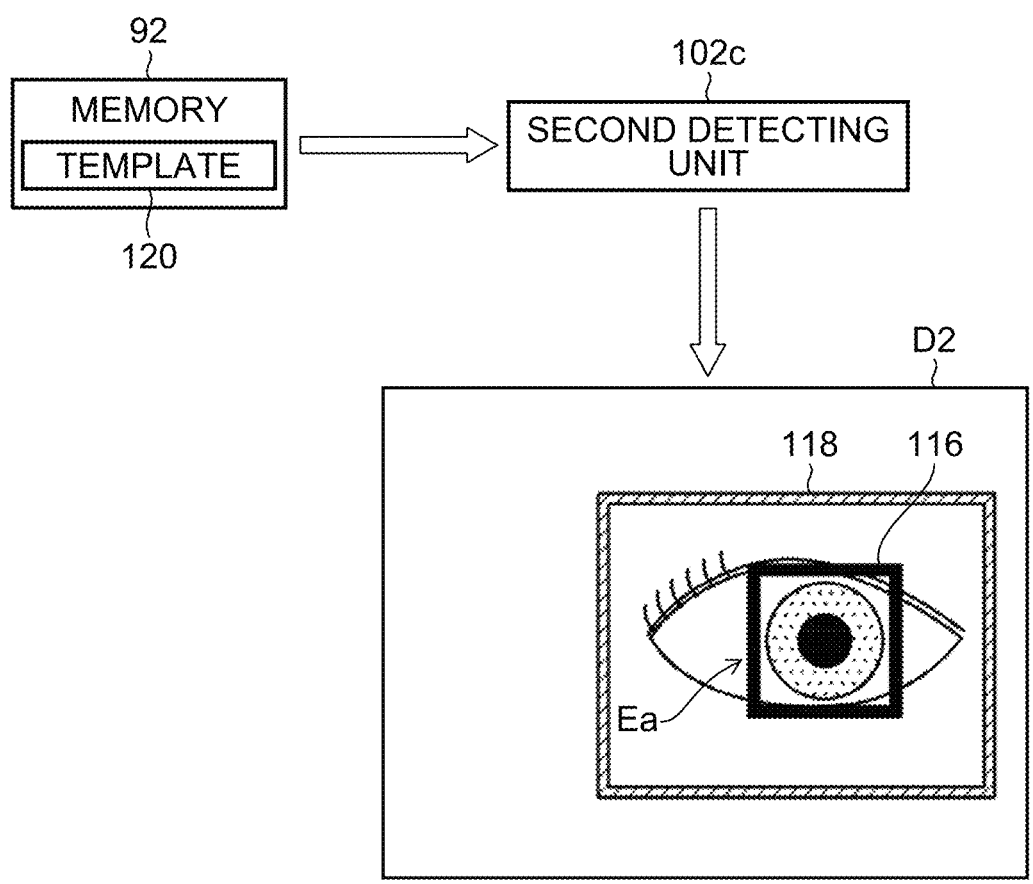
FIG. 8 is an explanatory drawing for describing a processing for detecting a pupil image from an anterior ocular segment image by a second detecting unit.

FIG. 8 is an explanatory drawing for describing a processing for detecting a pupil image 116 from the anterior ocular segment image D2 by a second detecting unit 102*c*. As illustrated in FIG. 8 and FIG. 5, the second detecting unit 102*c* detects the pupil image 116 from within the presence range 118 of the anterior ocular segment image D2 by known template matching, based on the template 120 (shape information 120*a* and presence range information 120*b*) stored in the memory 92. Specifically, the second detecting unit 102*c* identifies the presence range 118 within the anterior ocular segment image D2 based on the presence range information 120*b* and detects the pupil image 116 having a shape corresponding to the shape information 120*a* from within the presence range 118.

Instead of performing template matching, the second detecting unit 102*c* may detect the pupil image 116 from within the presence range 118 in the anterior ocular segment image D2, by performing the processing for detecting the pupil image 116 similar to that in the first detecting unit 102*a* described above.

The repetition controlling unit 102*d* repeatedly activates the first detecting unit 102*a*, the estimating unit 102*b*, and the second detecting unit 102*c* each time when the anterior ocular segment image acquiring unit 100 repeatedly acquires the anterior ocular segment images D1 and D2 from the first camera 20*a* and the second camera 20*b*.

Accordingly, detection of the pupil image 116 from the anterior ocular segment image D1 by the first detecting unit 102*a*, creation of the template 120 by the estimating unit 102*b*, and detection of the pupil image 116 from the anterior ocular segment image D2 (presence range 118) by the second detecting unit 102*c* are performed repeatedly.

Returning to FIG. 5, the determining unit 104 performs the face support determination based on the results of detection repeatedly performed by the second detecting unit 102*c*. Here, when the examinee's face is properly supported by the face supporting unit 12, the movement of his or her face is almost suppressed. Therefore, even if the pupil image 116 within the anterior ocular segment image D2 moves in the anterior ocular segment image D2 in response to the involuntary eye movement of the subject eye E, it remains within the presence range 118 for a certain period of time. Conversely, when the examinee's face is not properly supported by the face supporting unit 12, such as when the examinee's face is not in contact with the chin rest 12*a*, movement of his or her face occurs. Thus, the state in which the pupil image 116 remains within the presence range 118 of the anterior ocular segment image D2 does not continue for a certain period of time. Therefore, the determining unit 104 determines presence or absence of the movement of the face supported by the face supporting unit 12 for a certain period of time determined in advance based on the results of detection of repetition by the second detecting unit 102*c*, to perform face support determination for determining whether or not the face is properly supported by the face supporting unit 12.

Specifically, the determining unit 104 determines whether the number of times of consecutive detections of the pupil image 116 (the number of consecutive times when the pupil image 116 is consecutively detected) from within the presence range 118 of the anterior ocular segment image D2 reaches a predetermined number of times, based on the results of detection of repetition by the second detecting unit 102c. In other words, the determining unit 104 determines whether the detection of the pupil image 116 from within the presence range 118 lasts (continues) for a certain period of time or more based on the results of detection of repetition by the second detecting unit 102c.

In a case where the detection of the pupil image 116 from within the presence range 118 continues for a certain period of time or more, the determining unit 104 determines that there is no movement of the examinee's face supported by the face supporting unit 12. Thus, the determining unit 104 determines that the face is properly supported by the face supporting unit 12. Conversely, in a case where detection of the pupil image 116 from within the presence range 118 does not continue for the certain period of time or more, the determining unit 104 determines that there is a movement of the examinee's face supported by the face supporting unit 12, and thus determines that the face is not properly supported by the face supporting unit 12.

In a case where the determining unit 104 determines that the face is properly supported by the face supporting unit 12, the result of determination is output to the relative position detecting unit 108 and the alignment controlling unit 110. In a case where the determining unit 104 determines that the face is not properly supported by the face supporting unit 12, the result of determination is output to the notification controlling unit 106.

Figure 9:
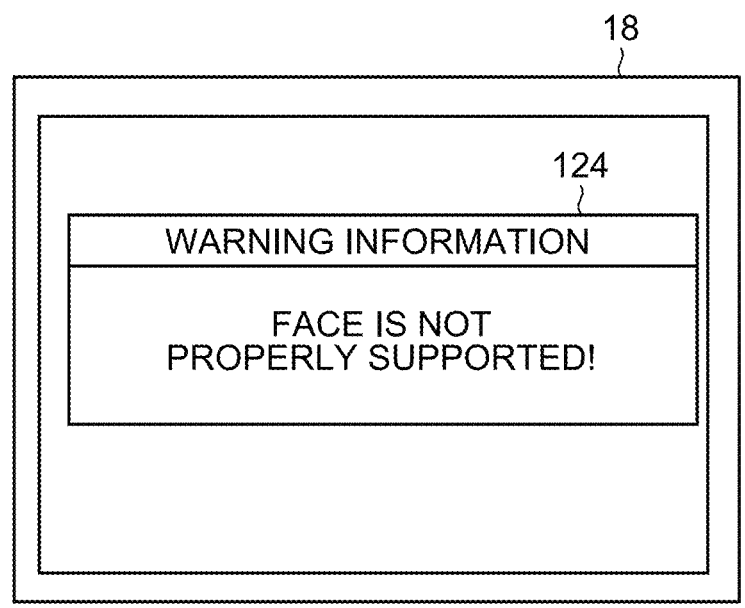
FIG. 9 is an explanatory drawing illustrating an example of a display of warning information by a monitor.

FIG. 9 is an explanatory drawing illustrating an example of a display (notification) of warning information 124 by a monitor 18. As illustrated in FIG. 9 and FIG. 5, the notification controlling unit 106 displays warning information 124 indicating that the face is not properly supported by the face supporting unit 12 on the monitor 18 when the result of determination from the determining unit 104 is input. This causes the warning information 124 to be reported to the examiner. Therefore, in this case, the notification controlling unit 106 and the monitor 18 function as the notifying unit of the present invention. A warning message may be output from a speaker (not illustrated) in place of displaying the warning information 124 by the monitor 18 or together with the displaying the warning information 124.

Figure 10:
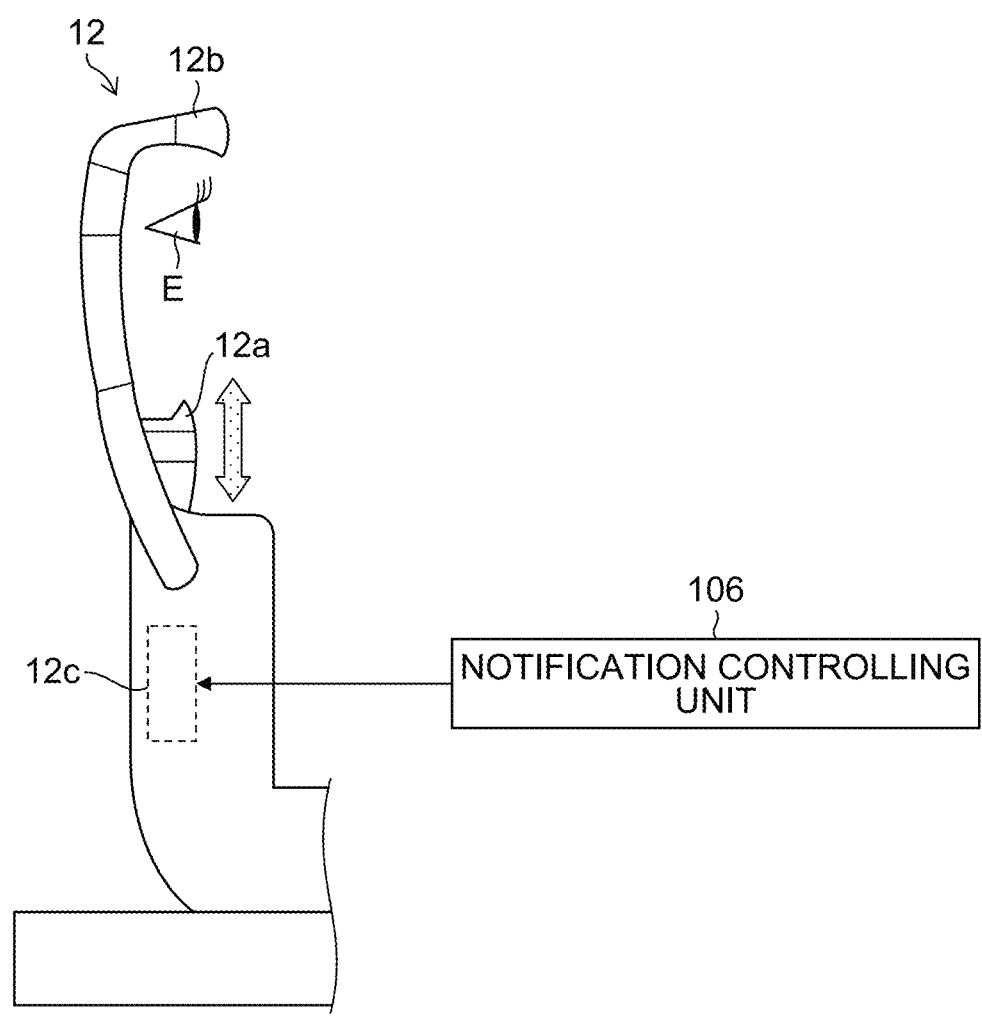
FIG. 10 is an explanatory drawing illustrating an example of notifying the examinee that the examinee's face is not properly supported by the face supporting unit.

FIG. 10 is an explanatory drawing illustrating an example of notifying the examinee that the examinee's face is not properly supported by the face supporting unit 12.

As illustrated in FIG. 10 and FIG. 5, when the result of determination from the determining unit 104 is input, the notification controlling unit 106 drives the motorized lifting mechanism 12c and moves, for example, a chin rest 12a and a forehead fit 12b up and down in the Y direction to change the face supporting position by the chin rest 12a, and so forth. This allows the examinee to be notified that the face is not properly supported by the face supporting unit 12. Accordingly, in this case, the notification controlling unit 106 and the face supporting unit 12 function as the notifying unit of the present invention.

[Auto-Alignment]

Returning to FIG. 5, the relative position detecting unit 108 and the alignment controlling unit 110 are used for auto-alignment and are operated by receiving an input of the result of determination from the determining unit 104.

The relative position detecting unit 108 detects the pupil image 116 (pupil region and pupil shape) from each of the anterior ocular segment images D1 and D2, based on the anterior ocular segment images D1 and D2 input from the anterior ocular segment image acquiring unit 100, and identifies characteristic position of each pupil image 116 corresponding to the pupil center or the corneal apex. Next, based on the positions and photographing magnifications of the first camera 20a and the second camera 20b, and the characteristic position of each of the anterior ocular segment images D1 and D2, the relative position detecting unit 108 calculates a relative position (3D position) of the subject eye E with respect to the measurement head 14 by a known method (see Japanese Patent Application Laid-Open No. 2013-248376). The relative position detecting unit 108 then outputs the result of calculation as the results of detection of the relative position of the subject eye E to the alignment controlling unit 110.

The processing for detecting the pupil images 116 from the anterior ocular segment images D1 and D2 by the relative position detecting unit 108 is precise processing which is required to accurately identify the characteristic positions described above, unlike the detection processing by the first detecting unit 102a in the face support determination described above. The relative position detecting unit 108, for example, binarizes the anterior ocular segment images D1 and D2, and precisely calculates the relative position of the subject eye E, from the binarized anterior ocular segment images D1 and D2.

The alignment controlling unit 110 drives the motorized driving mechanism 17 based on the result of detection of the relative position of the subject eye E by the relative position detecting unit 108 to perform the auto-alignment of the measurement head 14 with respect to the subject eye E.

[Acquisition of Ocular Characteristics]

After completion of the auto-alignment, the ocular characteristics acquisition controlling unit 112 operates to acquire the ocular characteristics of the subject eye E (fundus photographic images and OCT images of the fundus Ef). Specifically, the ocular characteristics acquisition controlling unit 112 drives the fundus camera unit 14a to acquire a fundus photographic image of the fundus Ef. In addition, the ocular characteristics acquisition controlling unit 112 drives the OCT optical system 80, the OCT unit 14b, and the image forming unit 94, and so forth to acquire the OCT image of fundus Ef.

[Operation of Ophthalmologic Device of First Embodiment]

Figure 11:
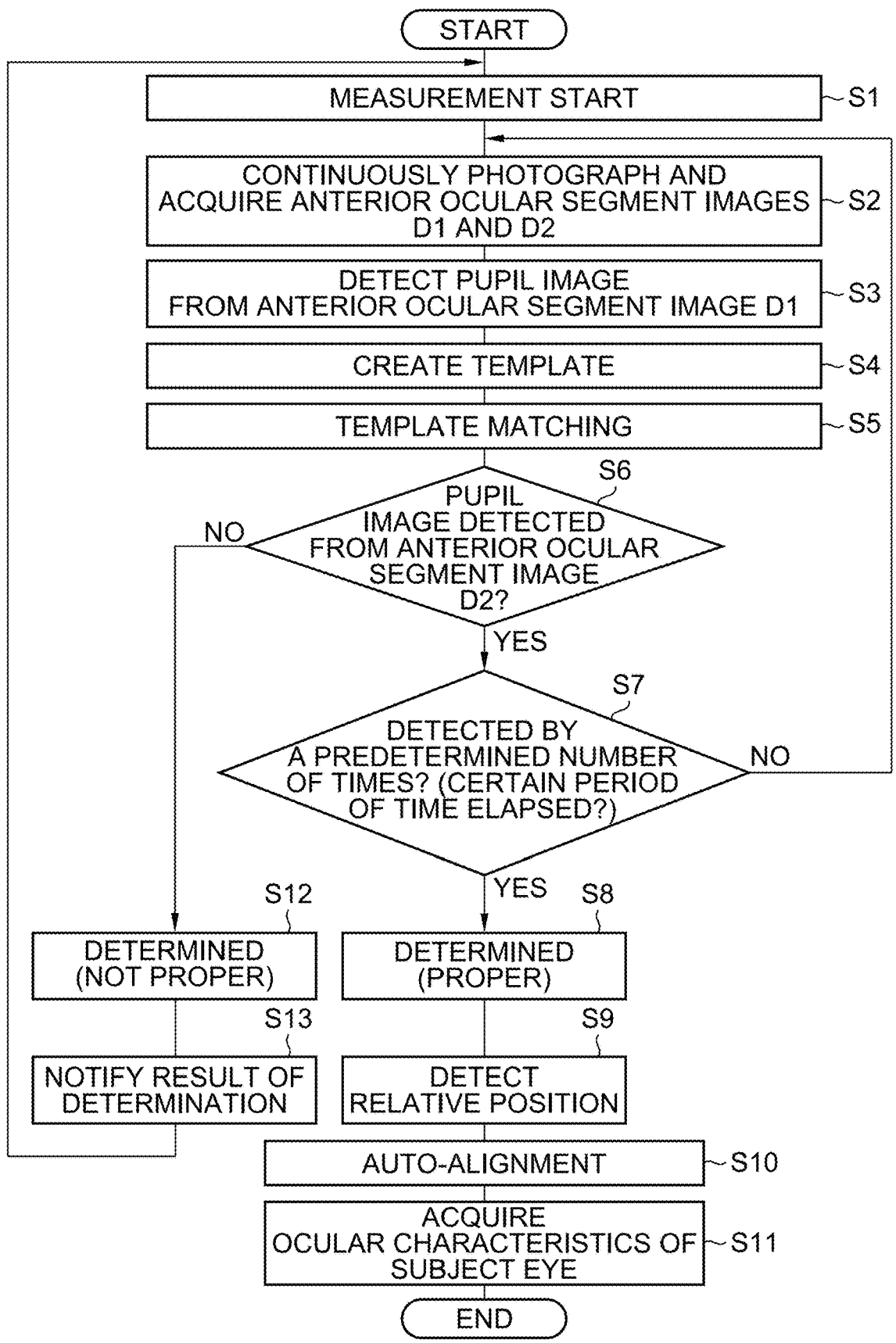
FIG. 11 is a flowchart showing a flow of processing for acquiring ocular characteristics from the subject eye, in particular, a face support determination processing by the ophthalmologic device according the first embodiment.

FIG. 11 is a flowchart showing a flow of processing for acquiring the ocular characteristics from the subject eye E by the ophthalmologic device 10 according to the first embodiment configured as described above, in particular, a flow of face support determination processing according to a method of controlling the ophthalmologic device 10 of the present invention. As illustrated in FIG. 11, when the power of the ophthalmologic device 10 is turned on by the examiner or when a measurement start operation (capture operation) is performed at the operating unit 16, the acquisition of the ocular characteristics of the subject eye E is started (Step S1).

The general controlling unit 90 causes the first camera 20a and the second camera 20b to start continuous photographing of the anterior ocular segment Ea of the subject eye E. As a result, the anterior ocular segment image acquiring unit 100 acquires anterior ocular segment images D1 and D2 from the first camera 20a and the second camera 20b, respectively, and outputs these anterior ocular segment images D1 and D2 to the pupil image detecting unit 102 (step S2, corresponding to the step of acquiring the anterior ocular segment images of the present invention).

When the anterior ocular segment images D1 and D2 are input to the pupil image detecting unit 102, the first detecting unit 102a performs, as illustrated in FIG. 6 described above, the binarization processing, labeling processing, and filtering processing on the anterior ocular segment image D1 to detect the pupil image 116 from the anterior ocular segment image D1 and output the results of detection of the position and the shape of the pupil image 116 to the estimating unit 102b (Step S3).

Next, as illustrated in FIG. 7 above, the estimating unit 102b estimates the shape and presence range 118 of the pupil image 116 within the anterior ocular segment image D2 based on the result of detection from the first detecting unit 102a to create the template 120 (the shape information 120a and the presence range information 120b) (Step S4). Then, as illustrated in FIG. 8 above, the second detecting unit 102c performs template matching based on the template 120 to detect the pupil image 116 from within the presence range 118 of the anterior ocular segment image D2 (Step S5).

In a case where the pupil image 116 is detected from within the presence range 118 of the anterior ocular segment image D2, the repetition controlling unit 102d causes a series of processing from Step S3 to Step S6 described above to be repeatedly performed (Yes in Step S6, No in Step S7). In case where the pupil image 116 is not detected from within the presence range 118 of the anterior ocular segment image D2, the procedure proceeds to Step S12 described below (No in Step S6). Steps S3 to S6 correspond to the pupil image detection step of the present invention.

Until determined to be Yes in Step S7 or No in Step S6, the repetition controlling unit 102d causes the series of processing from Step S3 to Step S6 to be repeatedly performed, each time when the anterior ocular segment image acquiring unit 100 repeatedly acquires the anterior ocular segment images D1 and D2 from the first camera 20a and the second camera 20b.

Based on the results of detection repeatedly performed by the second detecting unit 102c, in a case where the number of times of consecutive detections of the pupil image 116 from within the presence range 118 of the anterior ocular segment image D2 reaches a predetermined number of times, that is, in a case where detection of the pupil image 116 continues for a certain period of time or more, the determining unit 104 determines that the face is properly supported by the face supporting unit 12 (Yes in Step S7, Step S8). Note that Step S8, together with step S12 described below, corresponds to the determination step of the present invention. The determining unit 104 then outputs the result of determination that the face is properly supported by the face supporting unit 12 to the relative position detecting unit 108 and the alignment controlling unit 110. Thus, the auto-alignment automatically starts, following the face support determination.

The relative position detecting unit 108 detects the relative position of the subject eye E with respect to the measurement head 14 based on the anterior ocular segment images D1 and D2 input from the anterior ocular segment image acquiring unit 100, and outputs the result of detection to the alignment controlling unit 110 (Step S9). Accordingly, the alignment controlling unit 110 drives the motorized driving mechanism 17 based on the results of detection of the relative position of the subject eye E to perform the auto-alignment of the measurement head 14 with respect to the subject eye E (Step S10).

When the auto-alignment is completed, the ocular characteristics acquisition controlling unit 112 drives the fundus camera unit 14a to acquire a fundus photographic image of the fundus Ef, or drives the OCT optical system 80, the OCT unit 14b, the image forming unit 94, and so forth to acquire the OCT image of the fundus Ef. Accordingly, the acquisition of the ocular characteristics of the subject eye E is completed (Step S11).

On the other hand, in a case where the pupil image 116 is not detected by the second detecting unit 102c from within the presence range 118 of the anterior ocular segment image D2 (No, in Step S6), the determining unit 104 determines that the face is not properly supported by the face supporting unit 12 (Step S12). The determining unit 104 then outputs the result of determination that the face is not properly supported by the face supporting unit 12 to the notification controlling unit 106.

Upon reception of the result of determination input from the determining unit 104, the notification controlling unit 106 displays the warning information 124 on the monitor 18 or drives the motorized lifting mechanism 12c to move the chin rest 12a up and down in the Y direction as illustrated in FIG. 9 and FIG. 10 described above. Accordingly, the examiner and the examinee are notified that the examinee's face is not properly supported by the face supporting unit 12 (Step S13). The examiner then alerts the examinee so that the examinee's face is properly supported by the face supporting unit 12, or adjusts the position of the chin rest 12a, and so forth. Then, the series of processing from Step S1 onwards is repeatedly performed.

Effects and Advantages of the Embodiment

As described above, in this embodiment, whether the examinee's face is properly supported by the face supporting unit 12 can be determined based on the anterior ocular segment images D1 and D2 photographed by the stereo camera 20. Therefore, the ocular characteristics of the subject eye E can be acquired in a state in which the examinee's face is properly supported by the face supporting unit 12. This prevents the face from moving during the acquisition of the ocular characteristics of the subject eye E. Therefore, it is possible to prevent deterioration of the accuracy of the acquired ocular characteristics, or failure in acquisition of the ocular characteristics. In addition, since existing stereo cameras 20 can be used, face support determination can be performed with only software modifications. As a result, the ocular characteristics of the subject eye E can be acquired accurately and reliably.

In addition, since the face support determination and the auto-alignment can be performed using the anterior ocular segment images D1 and D2 photographed by the first camera 20a and the second camera 20b, the processing of the face support determination and the processing of the auto-alignment (detection of the relative position of the subject eye E) can be performed in parallel.

Second Embodiment

Next, the ophthalmologic device 10 according to the second embodiment will be described. The repetition controlling unit 102d of the pupil image detecting unit 102 according to the first embodiment described above repeatedly activates the first detecting unit 102a, the estimating unit 102b, and the second detecting unit 102c, each time when the anterior ocular segment image acquiring unit 100 repeatedly acquires the anterior ocular segment images D1 and D2 from the first camera 20a and the second camera 20b. Accordingly, detection (template matching) of the pupil image 116 from the anterior ocular segment image D1 by the first detecting unit 102a, creation of the template 120 by the estimating unit 102b, and detection of the pupil image 116 from the anterior ocular segment image D2 by the second detecting unit 102c are performed repeatedly.

In contrast, in the second embodiment, detection of the pupil image 116 from the anterior ocular segment image D2 for the second and subsequent times by the second detecting unit 102c (template matching) is performed repeatedly by using the template 120 generated based on the anterior ocular segment image D1 for the first time. Note that the ophthalmologic device 10 according to the second embodiment has the same basic configuration as the ophthalmologic device 10 according to the first embodiment described above, except that the functions of the anterior ocular segment image acquiring unit 100 and the repetition controlling unit 102d are different. Therefore, those having the same function or configuration as the first embodiment described above are designated by the same reference signs and description thereof will be omitted.

In face support determination processing, the anterior ocular segment image acquiring unit 100 according to the second embodiment performs: image acquisition processing for the first time for acquiring the anterior ocular segment images D1 and D2 from the first camera 20a and the second camera 20b; and image acquisition processing for the second and subsequent times for acquiring the anterior ocular segment image D2 repeatedly from the second camera 20b.

The repetition controlling unit 102d according to the second embodiment repeatedly activates the second detecting unit 102c, every time when the pupil image 116 is detected from within the presence range 118 of the anterior ocular segment image D2 by the second detecting unit 102c until the determination by the determining unit 104 is completed.

Figure 12:
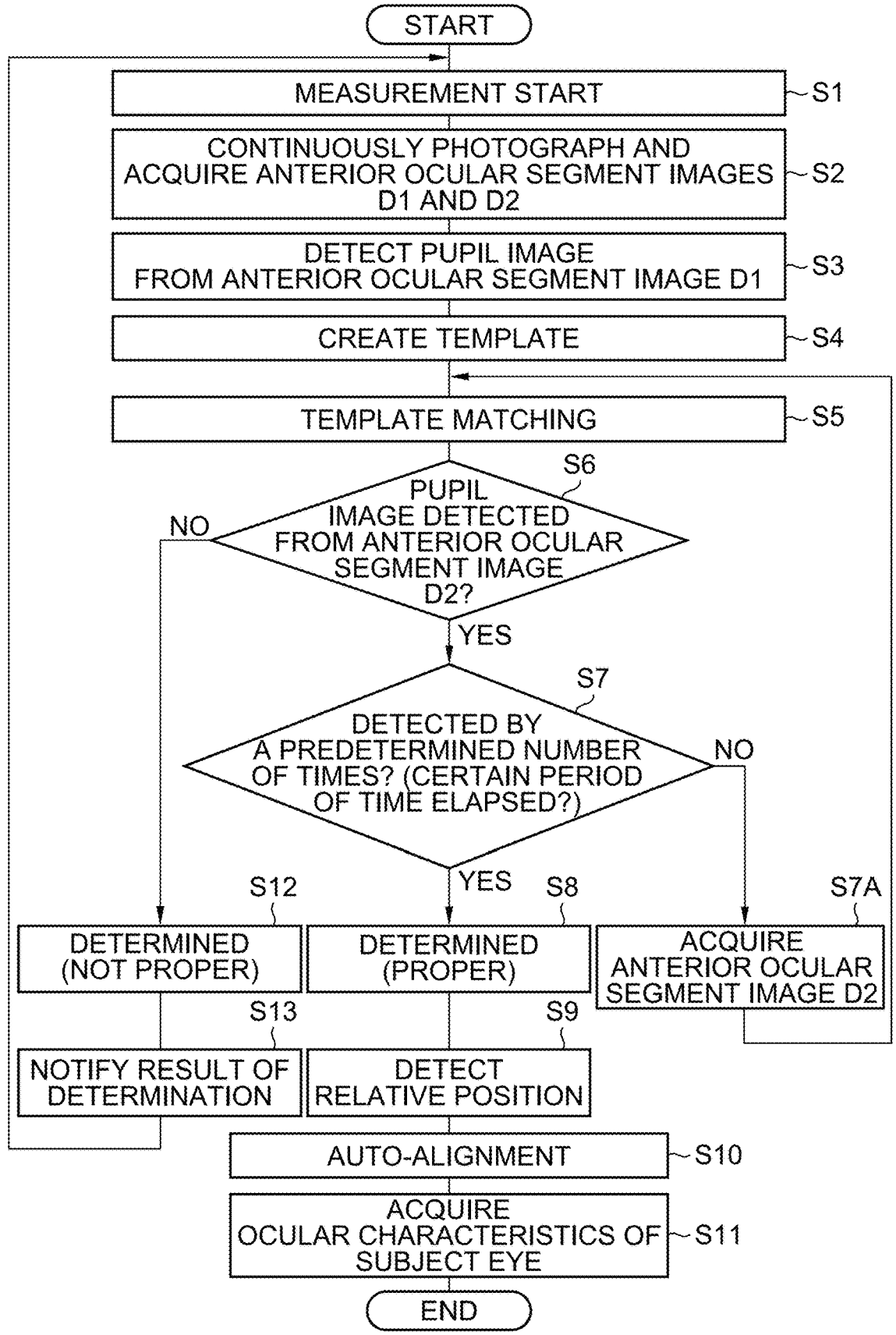
FIG. 12 is a flowchart showing a flow of processing for acquiring the ocular characteristics from the subject eye by an ophthalmologic device according to a second embodiment, in particular, a face support determination processing according to a method of controlling the ophthalmologic device of the present invention.

FIG. 12 is a flowchart showing a flow of processing for acquiring the ocular characteristics from the subject eye E by the ophthalmologic device 10 of the second embodiment, in particular, a flow of face support determination processing according to a method of controlling the ophthalmologic device 10 of the present invention. Note that processing from Step S1 to Step S7 and processing from Step S8 onward are basically the same as those in the first embodiment illustrated in FIG. 11 described above, and thus description will be omitted.

When the determination in Step S7 is No, the anterior ocular segment image acquiring unit 100 acquires an anterior ocular segment image D2 from the second camera 20b and outputs the anterior ocular segment image D2 to the second detecting unit 102c (Step S7A). In this case, the operation of the first camera 20a may be stopped or may not be stopped.

Next, the repetition controlling unit 102d according to the second embodiment repeatedly activates the second detecting unit 102c. Accordingly, the second detecting unit 102c performs template matching based on the template 120 created by the estimating unit 102b after the image acquisition processing for the first time, and detects the pupil image 116 from the anterior ocular segment image D2 acquired by the image acquisition processing for the second time (Steps S5 and S6).

Then, until the determination in Step S7 is Yes or until the determination in Step S6 is No, the processing in Step S7A by the anterior ocular segment image acquiring unit 100 and the processing in Steps S5 and S6 by the second detecting unit 102c are repeatedly performed.

In this manner, in the second embodiment, after the processing of the image acquisition for the first time, the pupil images 116 can be detected from the anterior ocular segment images D2 acquired in the image acquisition processing for the second and subsequent times, based on the template 120 created by the estimating unit 102b. Accordingly, in the face support determination processing for the second and subsequent times, it is possible to omit the acquisition of the anterior ocular segment image D1, the detection of the pupil image 116 from the anterior ocular segment image D1, and the creation of the template 120. As a result, time required for face support determination processing is reduced in the second and subsequent times.

Third Embodiment

Figure 13:
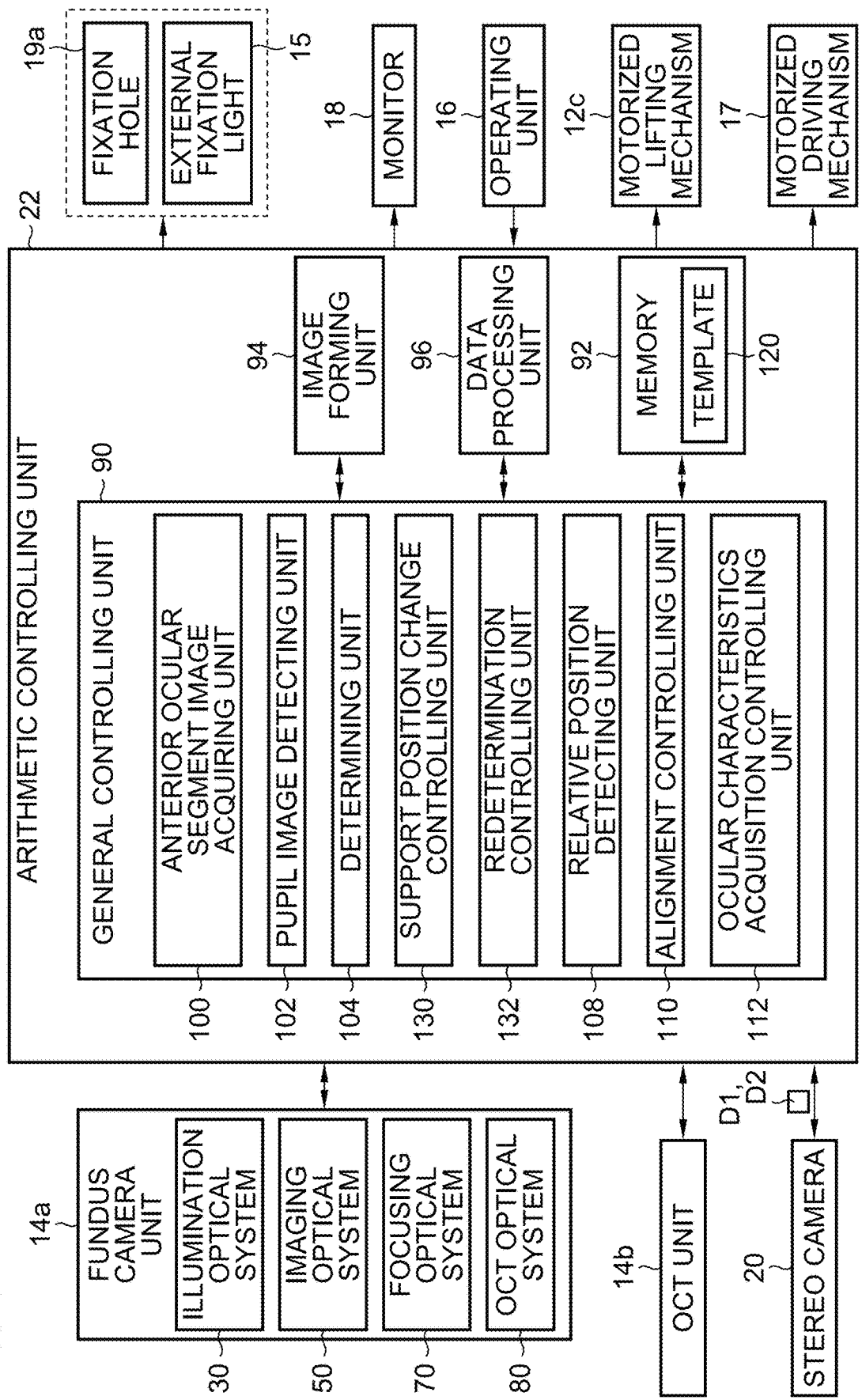
FIG. 13 is a functional block diagram of an arithmetic controlling unit of the ophthalmologic device according to a third embodiment.

FIG. 13 is a functional block diagram of an arithmetic controlling unit 22 of the ophthalmologic device 10 according to a third embodiment. In each of the embodiments described above, the notification controlling unit 106 performs a notification of the result of determination in a case where it is determined by the determining unit 104 that the examinee's face is not properly supported by the face supporting unit 12. In contrast, in the ophthalmologic device 10 according to the third embodiment, in a case where the determining unit 104 determines that the examinee's face is not properly supported by the face supporting unit 12, the face support determination processing is performed again after the face supporting position is changed by the chin rest 12a or the like.

As illustrated in FIG. 13, the ophthalmologic device 10 according to the third embodiment has a configuration which is basically the same as that of the ophthalmologic device 10 of each of the embodiments described above, except that the general controlling unit 90 further functions as a supporting position change controlling unit 130 and a redetermination controlling unit 132. Therefore, those having the same function or configuration as each embodiment described above are designated by the same reference signs and description thereof will be omitted.

Figure 14:
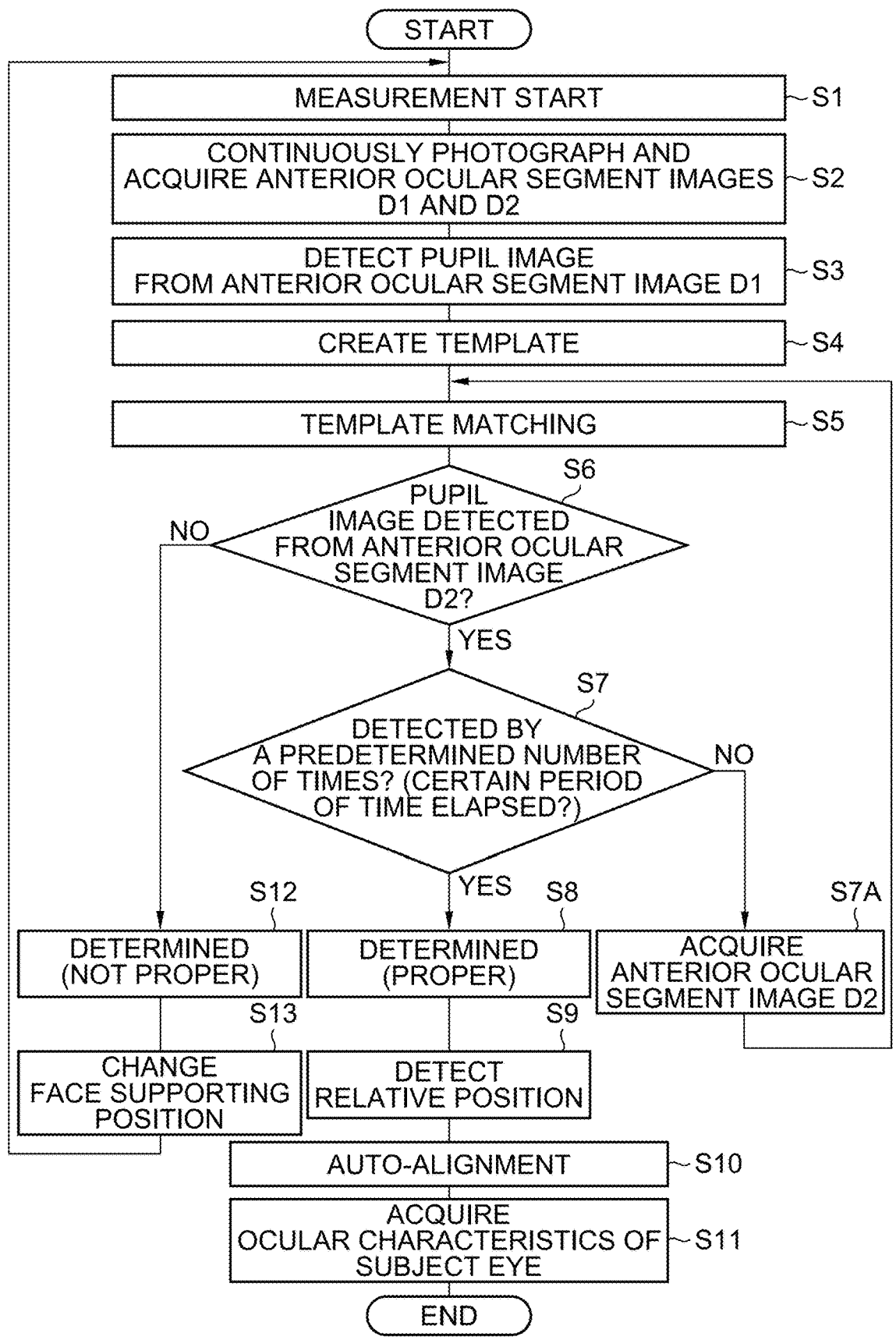
FIG. 14 is a flowchart showing a flow of processing for acquiring the ocular characteristics from the subject eye by an ophthalmologic device according to a third embodiment, in particular, a face support determination processing according to a method of controlling the ophthalmologic device of the present invention.

FIG. 14 is a flowchart showing a flow of processing for acquiring the ocular characteristics from the subject eye E by an ophthalmologic device 10 according to the third embodiment, in particular, a flow of face support determination processing according to a method of controlling the ophthalmologic device 10 of the present invention. Note that the series of processing from step S1 to step S12 is basically the same as the processing in the second embodiment illustrated in FIG. 12 described above, so the specific explanation will be omitted.

As illustrated in FIG. 13 and FIG. 14, in a case where the determining unit 104 determines that the face is not properly supported by the face supporting unit 12 (Step S12), the supporting position change controlling unit 130 is activated. This supporting position change controlling unit 130 drives the motorized lifting mechanism 12c to change the supporting position of the examinee's face by the face supporting unit 12, for example, to change, the supporting position of the examinee's face upward in the Y direction (Step S14).

For example, the supporting position change controlling unit 130 drives the motorized lifting mechanism 12c to raise the face supporting position by the face supporting unit 12 by approximately 5 mm. Alternatively, the supporting position change controlling unit 130 monitors (detects) the position of the pupil image 116 in at least one of the anterior ocular segment images D1 and D2 acquired by the anterior ocular segment image acquiring unit 100 and drives the motorized lifting mechanism 12c to change the supporting position of the face supported by the face supporting unit 12 at a low speed upward in the Y direction, until the position of the pupil image 116 changes. In place of changing the supporting position of the examinee's face upward in the Y direction, it may be changed downward.

In this manner, by changing the supporting position of the examinee's face by the face supporting unit 12, in particular upwardly in the Y direction, the support of the examinee's face by the face supporting unit 12 may be changed from an improper state to a proper state, or the examinee can be alerted that the face is not properly supported by the face supporting unit 12.

In a case where the face supporting position by the face supporting unit 12 is changed, the redetermination controlling unit 132 controls each unit (the anterior ocular segment image acquiring unit 100, the pupil image detecting unit 102, and the determining unit 104) of the general controlling unit 90 to repeatedly perform the series of processing from the Steps S1 to S7A described above. Accordingly, the face support determination processing described in the second embodiment described above is repeatedly performed. As in the first embodiment illustrated in FIG. 11 above, the series of processing from Step S1 to Step S7 described above may be repeatedly performed.

From then onward until the determining unit 104 determines that the face is properly supported by the face supporting unit 12, the series of processing from Step S14, from Step S1 to Step S7A (Step S7) is repeatedly performed.

In this manner, in the third embodiment, even in a case where the examinee's face is not properly supported by the face supporting unit 12, the face support determination processing is repeatedly performed after changing the face supporting position by the face supporting unit 12. Thus, the ophthalmologic device 10 can automatically proceed to the subsequent processing (Step S9 to S11) without any operations performed by the examiner. Accordingly, the time and effort of the examiner can be alleviated.

Others

In each of the embodiments described above, the stereo camera 20 (a first camera 20a and a second camera 20b) has been described as an example, but a plurality, three or more, of cameras may be used to photograph the subject eye E. In this case as well, the anterior ocular segment image acquiring unit 100 acquires the anterior ocular segment image D1 photographed by the first camera 20a among the plurality of cameras and the anterior ocular segment image D2 taken by one or more second cameras 20b among the plurality of cameras repeatedly. In addition, the first detecting unit 102a detects the pupil image 116 for each anterior ocular segment image D1 photographed by the first camera 20a. Furthermore, the estimating unit 102b estimates the presence range 118 (creates the template 120) for each anterior ocular segment image D2 photographed by the one or more of the second cameras 20b. Moreover, the second detecting unit 102c detects the pupil image 116 from within the presence range 118 for each of the one or more anterior ocular segment images D2. Then, the determining unit 104 determines whether the number of times of consecutive detections of the pupil image 116 from within the presence range 118 for each of one or more of the anterior ocular segment images D2 has reached a predetermined number of times.

In each of the embodiments described above, the detection of the pupil image 116 for each of the anterior ocular segment images D1 and D2 by the pupil image detecting unit 102 and the face support determination by the determining unit 104 are performed based on the anterior ocular segment images D1 and D2 continuously photographed by the first camera 20a and the second camera 20b. However, the number of cameras used for the face support determination may be one.

In this case, the anterior ocular segment image acquiring unit 100 repeatedly acquires the anterior ocular segment image D1 or the anterior ocular segment image D2 (hereinafter, referred to as a single anterior ocular segment image) continuously photographed by either one of the first camera 20a and the second camera 20b. The pupil image detecting unit 102 repeatedly detects the pupil image 116 for each single anterior ocular segment image. The determining unit 104 then performs a face support determination based on whether the state in which the position of the pupil image 116 within the single anterior ocular segment image remains in the range corresponding to the involuntary eye movement of the subject eye E (corresponding to the previously described presence range 118) continues for a certain period of time. Accordingly, face support determination can be performed by using a single camera.

In this case, the anterior ocular segment image acquiring unit 100 may repeatedly acquire the observation image of the anterior ocular segment Ea from the imaging optical system 50 (corresponding to the anterior ocular segment observation system of the present invention) capable of continuously photographing the anterior ocular segment Ea through the objective lens 43. In this case as well, the face support determination can be performed in the same manner as the case where either one of the first camera 20a and the second camera 20b is used.

In each of the embodiments described above, the arithmetic controlling unit 22 is built in the measurement head 14. However, it may be provided externally of the base 11 and the measurement head 14, and so forth. In other words, the ophthalmologic device 10 of the present invention is also applicable to an apparatus for remote medical examination.

In each of the embodiments described above, the acquisition of a fundus photographic image and an OCT image of the fundus Ef has been described as an example of the acquisition of ocular characteristics of the subject eye E. However, the present invention can also be applied to the ophthalmologic device 10 for acquiring various ocular characteristics such as an ocular refractive power, an intraocular pressure, the number of corneal endothelial cells, and corneal shape of the subject eye E.

EXPLANATION OF REFERENCE SIGNS

10 . . . ophthalmologic device
12 . . . face supporting unit
12a . . . chin rest
12b . . . forehead fit
12c . . . motorized lifting mechanism
14 . . . measurement head
14a . . . fundus camera unit
14b . . . OCT unit
16 . . . operating unit
17 . . . motorized driving mechanism
18 . . . monitor
20 . . . stereo camera
20a . . . first camera
20b . . . second camera
22 . . . arithmetic controlling unit
30 . . . illumination optical system
43 . . . objective lens
50 . . . imaging optical system
70 . . . focusing optical system 80 . . . OCT optical system
90 . . . general controlling unit
100 . . . anterior ocular segment image acquiring unit
102 . . . pupil image detecting unit
102a . . . first detecting unit
102b . . . estimating unit
102c . . . second detecting unit
102d . . . repetition controlling unit
104 . . . determining unit
106 . . . notification controlling unit
108 . . . relative position detecting unit
110 . . . alignment controlling unit
112 . . . ocular characteristics acquisition controlling unit
116 . . . pupil image
118 . . . presence range
120 . . . template
120a . . . shape information
120b . . . presence range information
124 . . . warning information
D1, D2 . . . anterior ocular segment image
E . . . subject eye
Ea . . . anterior ocular segment
Ef . . . fundus

What is claimed is:

1. An ophthalmologic device comprising:
a face support configured to support a face of an examinee;
processing circuitry configured as an anterior ocular segment image acquiring unit configured to repeatedly acquire an anterior ocular segment image of a subject eye of the face supported by the face support;
the processing circuitry further configured as a pupil image detecting unit configured to detect a pupil image of the subject eye for each anterior ocular segment image based on the anterior ocular segment image repeatedly acquired by the anterior ocular segment image acquiring unit; and
the processing circuitry further configured as a determining unit configured to determine whether or not the face is properly supported by the face support based on a result of detection of the pupil image for each anterior ocular segment image by the pupil image detecting unit, wherein
the anterior ocular segment image acquiring unit repeatedly acquires anterior ocular segment images from a plurality of cameras configured to photograph the subject eye from different directions, and
the processing circuitry is further configured as
a first detecting unit configured to detect the pupil image from the anterior ocular segment image photographed by a first camera among the plurality of cameras;
an estimating unit configured to estimate a presence range of the pupil image included in the anterior ocular segment image photographed by a second camera, which is different from the first camera among the plurality of cameras, the pupil image moving in response to involuntary eye movement of the subject eye, based on a result of detection by the first detecting unit;
a second detecting unit configured to detect the pupil image from within the presence range of the anterior ocular segment image photographed by the second camera based on a result of estimation by the estimating unit; and
a repetition controlling unit configured to repeatedly activate the first detecting unit, the estimating unit, and the second detecting unit each time when the anterior ocular segment image acquiring unit repeatedly acquires the anterior ocular segment images, and
the determining unit determines whether or not the face is properly supported by the face support based on results of detection repeatedly performed by the second detecting unit.

2. The ophthalmologic device according to claim 1, wherein
the determining unit determines, based on the results of detection repeatedly performed by the second detecting unit, that the face is properly supported by the face support in a case where the detection of the pupil image in the presence range continues for a certain period of time, which is determined in advance, or more, and determines that the face is not properly supported by the face support in a case where the detection of the pupil image in the presence range does not continue for the certain period of time or more.

3. The ophthalmologic device according to claim 1, wherein
the estimating unit creates a template indicating the presence range and a shape of the pupil image from the anterior ocular segment image photographed by the first camera based on the result of detection by the first detecting unit, and
the second detecting unit detects the pupil image from within the presence range of the anterior ocular segment image photographed by the second camera by template matching based on the template created by the estimating unit.

4. The ophthalmologic device according to claim 1, wherein the processing circuitry is further configured as:
an ocular characteristic acquiring unit configured to acquire ocular characteristics of the subject eye through an objective lens,
an ophthalmologic device main body configured to accommodate the ocular characteristic acquiring unit;
a relative movement mechanism configured to move the ophthalmologic device main body with respect to the subject eye;
a relative position detecting unit configured to detect a relative position of the subject eye relative to the ophthalmologic device main body based on the anterior ocular segment image acquired by the anterior ocular segment image acquiring unit; and
an alignment controlling unit configured to drive the relative movement mechanism to perform alignment of the ophthalmologic device main body relative to the subject eye based on a result of detection by the relative position detecting unit.

5. The ophthalmologic device according to claim 1, comprising wherein the processing circuitry is further configured as
a notifying unit configured to notify a result of determination by the determining unit in a case where the determining unit determines that the face is not properly supported by the face support.

6. The ophthalmologic device according to claim 5, comprising
a supporting position changing mechanism including a motor and configured to change a face supporting position by the face support, wherein
the notifying unit drives the supporting position changing mechanism to change the supporting position.

7. The ophthalmologic device according to claim 1, comprising:
- a supporting position changing mechanism including a motor and configured to change a face supporting position by the face support;
- the processing circuitry further configured as a supporting position change controlling unit configured to drive the supporting position changing mechanism and change the face supporting position in a case where the determining unit determines that the face is not properly supported by the face support, and
- the processing circuitry further configured as a redetermination controlling unit configured to repeatedly activate the anterior ocular segment image acquiring unit, the pupil image detecting unit, and the determining unit in a case where the face supporting position is changed by the supporting position changing mechanism.

8. An ophthalmologic device comprising:
- a face support configured to support a face of an examinee;
- processing circuitry configured as an anterior ocular segment image acquiring unit configured to repeatedly acquire an anterior ocular segment image of a subject eye of the face supported by the face support;
- the processing circuitry further configured as a pupil image detecting unit configured to detect a pupil image of the subject eye for each anterior ocular segment image based on the anterior ocular segment image repeatedly acquired by the anterior ocular segment image acquiring unit; and
- the processing circuitry further configured as a determining unit configured to determine whether or not the face is properly supported by the face support based on a result of detection of the pupil image for each anterior ocular segment image by the pupil image detecting unit, wherein the anterior ocular segment image acquiring unit performs:
- image acquisition processing for the first time for acquiring anterior ocular segment images from the first camera and the second camera which photograph the subject eye from directions different from each other; and
- image acquisition processing for the second and subsequent times for acquiring the anterior ocular segment image repeatedly from the second camera, and the processing circuitry is further configured as
- a first detecting unit configured to detect the pupil image from the anterior ocular segment image acquired by the anterior ocular segment image acquiring unit from the first camera in the first image acquisition processing;
- an estimating unit configured to estimate a presence range of the pupil image included in the anterior ocular segment image acquired from the second camera by the anterior ocular segment image acquiring unit, the pupil image moving in response to the involuntary eye movement of the subject eye, based on a result of detection by the first detecting unit;
- a second detecting unit configured to detect the pupil image from within the presence range of the anterior ocular segment image acquired by the anterior ocular segment image acquiring unit from the second camera based on a result of estimation by the estimating unit; and
- a repetition controlling unit configured to repeatedly activate the second detecting unit each time when the anterior ocular segment image acquiring unit repeatedly acquires the anterior ocular segment image from the second camera in the image acquisition processing for the second and subsequent times, and
- the determining unit determines whether or not the face is properly supported by the face support based on results of detection repeatedly performed by the second detecting unit.

9. The ophthalmologic device according to claim 8, wherein
the determining unit determines, based on the results of detection repeatedly performed by the second detecting unit, that the face is properly supported by the face support in a case where the detection of the pupil image in the presence range continues for a certain period of time, which is determined in advance, or more, and determines that the face is not properly supported by the face support in a case where the detection of the pupil image in the presence range does not continue for the certain period of time or more.

10. The ophthalmologic device according to claim 8, wherein
the estimating unit creates a template indicating the presence range and a shape of the pupil image from the anterior ocular segment image photographed by the first camera based on the result of detection by the first detecting unit, and
the second detecting unit detects the pupil image from within the presence range of the anterior ocular segment image photographed by the second camera by template matching based on the template created by the estimating unit.

11. The ophthalmologic device according to claim 8, wherein the processing circuitry is further configured as:
- an ocular characteristic acquiring unit configured to acquire ocular characteristics of the subject eye through an objective lens,
- an ophthalmologic device main body configured to accommodate the ocular characteristic acquiring unit;
- a relative movement mechanism configured to move the ophthalmologic device main body with respect to the subject eye;
- a relative position detecting unit configured to detect a relative position of the subject eye relative to the ophthalmologic device main body based on the anterior ocular segment image acquired by the anterior ocular segment image acquiring unit; and
- an alignment controlling unit configured to drive the relative movement mechanism to perform alignment of the ophthalmologic device main body relative to the subject eye based on a result of detection by the relative position detecting unit.

12. The ophthalmologic device according to claim 8, wherein the processing circuitry is further configured as
a notifying unit configured to notify a result of determination by the determining unit in a case where the determining unit determines that the face is not properly supported by the face support.

13. The ophthalmologic device according to claim 12, comprising
a supporting position changing mechanism including a motor and configured to change a face supporting position by the face support, wherein
the notifying unit drives the supporting position changing mechanism to change the supporting position.

14. The ophthalmologic device according to claim 8, comprising:

a supporting position changing mechanism including a motor and configured to change a face supporting position by the face support;

the processing circuitry further configured as a supporting position change controlling unit configured to drive the supporting position changing mechanism and change the face supporting position in a case where the determining unit determines that the face is not properly supported by the face support, and the processing circuitry further configured as a redetermination controlling unit configured to repeatedly activate the anterior ocular segment image acquiring unit, the pupil image detecting unit, and the determining unit in a case where the face supporting position is changed by the supporting position changing mechanism.

15. A method of controlling an ophthalmologic device comprising:

an anterior ocular segment image acquisition step of repeatedly acquiring an anterior ocular segment image of a subject eye of a face supported by a face support configured to support the face of an examinee;

a pupil image detection step of detecting a pupil image of the subject eye for each anterior ocular segment image based on the anterior ocular segment image repeatedly acquired by the anterior ocular segment image acquisition step; and a determination step of determining whether or not the face is properly supported by the face support based on a result of detection of the pupil image for each anterior ocular segment image by the pupil image detection step, wherein the anterior ocular segment image acquisition step repeatedly acquires anterior ocular segment images from a plurality of cameras configured to photograph the subject eye from different directions, and the pupil image detection step includes:

a first detecting step of detecting the pupil image from the anterior ocular segment image photographed by a first camera among the plurality of cameras;

estimating a presence range of the pupil image included in the anterior ocular segment image photographed by a second camera, which is different from the first camera among the plurality of cameras, the pupil image moving in response to involuntary eye movement of the subject eye, based on a result of detection by the detecting;

a second detecting step of detecting the pupil image from within the presence range of the anterior ocular segment image photographed by the second camera based on a result of estimating; and repeatedly activating the first detecting step, the estimating, and the second detecting step each time when the anterior ocular segment image acquisition step repeatedly acquires the anterior ocular segment images, and the determination step determines whether or not the face is properly supported by the face support based on results of detection repeatedly performed by the second detecting step.

16. A method of controlling an ophthalmologic device comprising:

an anterior ocular segment image acquisition step of repeatedly acquiring an anterior ocular segment image of a subject eye of a face supported by a face support configured to support the face of an examinee;

a pupil image detection step of detecting a pupil image of the subject eye for each anterior ocular segment image based on the anterior ocular segment image repeatedly acquired by the anterior ocular segment image acquisition step; and a determination step of determining whether or not the face is properly supported by the face support based on a result of detection of the pupil image for each anterior ocular segment image by the pupil image detection step, wherein the anterior ocular segment image acquisition step performs:

image acquisition processing for the first time for acquiring anterior ocular segment images from the first camera and the second camera which photograph the subject eye from directions different from each other; and image acquisition processing for the second and subsequent times for acquiring the anterior ocular segment image repeatedly from the second camera, and the pupil image detecting step includes:

a first detecting step to detect the pupil image from the anterior ocular segment image acquired by the anterior ocular segment image acquisition step from the first camera in the first image acquisition processing;

estimating a presence range of the pupil image included in the anterior ocular segment image acquired from the second camera by the anterior ocular segment image acquisition step, the pupil image moving in response to the involuntary eye movement of the subject eye, based on a result of detection by the first detecting step;

a second detecting step to detect the pupil image from within the presence range of the anterior ocular segment image acquired by the anterior ocular segment image acquisition step from the second camera based on a result of estimation by the estimating; and repeatedly activating the second detecting step each time when the anterior ocular segment image acquisition step repeatedly acquires the anterior ocular segment image from the second camera in the image acquisition processing for the second and subsequent times, and the determination step determines whether or not the face is properly supported by the face support based on results of detection repeatedly performed by the second detecting step.

* * * * *